(12) United States Patent
Pratt et al.

(10) Patent No.: US 12,119,087 B2
(45) Date of Patent: *Oct. 15, 2024

(54) METHODS AND SYSTEMS FOR SEQUENCE CALLING

(71) Applicant: ULTIMA GENOMICS, INC., Newark, CA (US)

(72) Inventors: Mark Pratt, Bozeman, MT (US); Gilad Almogy, Palo Alto, CA (US); Avishai Bartov, Hod-Hasharon (IL)

(73) Assignee: ULTIMA GENOMICS, INC., Fremont, CA (US)

( * ) Notice: Subject to any disclaimer, the term of this patent is extended or adjusted under 35 U.S.C. 154(b) by 110 days.

This patent is subject to a terminal disclaimer.

(21) Appl. No.: 17/574,260

(22) Filed: Jan. 12, 2022

(65) Prior Publication Data

US 2022/0199201 A1 Jun. 23, 2022

Related U.S. Application Data

(63) Continuation of application No. 17/406,464, filed on Aug. 19, 2021, now Pat. No. 11,276,480, which is a continuation of application No. 17/090,176, filed on Nov. 5, 2020, now Pat. No. 11,107,554, which is a continuation of application No. 16/845,278, filed on Apr. 10, 2020, which is a continuation of application No. PCT/US2018/057340, filed on Oct. 24, 2018.

(60) Provisional application No. 62/577,450, filed on Oct. 26, 2017.

(51) Int. Cl.
| | |
|---|---|
| *G16B 40/10* | (2019.01) |
| *C12Q 1/6806* | (2018.01) |
| *C12Q 1/6869* | (2018.01) |
| *G16B 30/10* | (2019.01) |
| *G16B 45/00* | (2019.01) |

(52) U.S. Cl.
CPC ........... *G16B 40/10* (2019.02); *C12Q 1/6806* (2013.01); *C12Q 1/6869* (2013.01); *G16B 30/10* (2019.02); *G16B 45/00* (2019.02)

(58) Field of Classification Search
CPC ........ G16B 40/10; G16B 30/10; G16B 45/00; C12Q 1/6806; C12Q 1/6869
See application file for complete search history.

(56) References Cited

U.S. PATENT DOCUMENTS

| | | |
|---|---|---|
| 4,666,828 A | 5/1987 | Gusella |
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson et al. |
| 5,409,811 A | 4/1995 | Tabor et al. |
| 5,641,658 A | 6/1997 | Adams et al. |
| 5,674,716 A | 10/1997 | Tabor et al. |
| 8,772,473 B2 | 7/2014 | Huang et al. |
| 10,344,328 B2 | 7/2019 | Barbee et al. |
| 11,107,554 B2 | 8/2021 | Pratt et al. |
| 11,276,480 B2 | 3/2022 | Pratt et al. |
| 2006/0136144 A1 | 6/2006 | Kamentsky |
| 2010/0169026 A1 | 7/2010 | Sorenson et al. |
| 2014/0121985 A1 | 5/2014 | Sayood et al. |
| 2014/0228223 A1 | 8/2014 | Gnirke et al. |
| 2014/0316716 A1 | 10/2014 | Jiang et al. |
| 2015/0118685 A1 | 4/2015 | Clark et al. |
| 2017/0044606 A1 | 2/2017 | Lo et al. |
| 2018/0373832 A1 | 12/2018 | Sakarya et al. |
| 2019/0078155 A1 | 3/2019 | Gordon |
| 2019/0147981 A1 | 5/2019 | Van Rooyen et al. |
| 2020/0097835 A1 | 3/2020 | Silver et al. |
| 2020/0303039 A1 | 9/2020 | Pratt et al. |
| 2021/0142869 A1 | 5/2021 | Pratt et al. |
| 2021/0363572 A1 | 11/2021 | Lee et al. |
| 2021/0366576 A1 | 11/2021 | Bartov et al. |
| 2021/0383895 A1 | 12/2021 | Pratt et al. |

FOREIGN PATENT DOCUMENTS

| | | |
|---|---|---|
| CN | 105980578 B | 2/2020 |
| WO | WO-2008009751 A2 | 7/2008 |
| WO | WO-2017053446 A2 | 3/2017 |
| WO | WO-2019084158 A1 | 5/2019 |
| WO | WO-2020185790 A1 | 9/2020 |
| WO | WO-2020227137 A1 | 11/2020 |
| WO | WO-2021007495 A1 | 1/2021 |
| WO | WO-2022056296 A1 | 3/2022 |

OTHER PUBLICATIONS

EP18870560.2 Extended European Search Report dated Nov. 12, 2021.
Feng et al., Improving alignment accuracy on homopolymer regions for semiconductor-based sequencing technologies; BMC Genomics, vol. 17, suppl. 7, art. 521, pp. 87-93 (2016).
Kretschy et al., Sequence-Dependent Fluorescence of Cy3- and Cy5-Labeled Double-Stranded DNA, Bioconjugate Chem., vol. 27, No. 3, pp. 840-848 (2016).
Miller, et al., Aggressive assembly of pyrosequencing reads with mates, Bioinformatics, vol. 24, No. 24, Oct. 24, 2008 (Oct. 24, 2008), pp. 2818-2824, XP055217082, ISSN: 1367-4803, DOI: 10.1093/bioinformatics/btn548.
PCT/US18/57340 Search Report & Written Opinion dated Feb. 15, 2019.
Shendure et al. Next-generation DNA sequencing. Nature Biotechnology 26:1135-1145. (Oct. 9, 2008).

(Continued)

*Primary Examiner* — Larry D Riggs, II
*Assistant Examiner* — Kettip Kriangchaivech
(74) *Attorney, Agent, or Firm* — Schmidt Patent Law, Inc.

(57) ABSTRACT

The present disclosure provides methods and systems for accurate and efficient context-aware base calling of sequences. In an aspect, disclosed herein is a method for sequencing a nucleic acid molecule, comprising: (a) sequencing the nucleic acid molecule to generate a plurality of sequence signals; and (b) determining base calls of the nucleic acid molecule based at least in part on (i) the plurality of sequence signals and (ii) quantified context dependency for at least a portion of the plurality of sequence signals.

20 Claims, 8 Drawing Sheets

Specification includes a Sequence Listing.

(56) References Cited

OTHER PUBLICATIONS

Tabor, S. et al., "A single residue in DNA polymerases of the *Escherichia coli* DNA polymerase I family is critical for distinguishing between deoxy- and dideoxyribonucleotides," PNAS, 1995, vol. 92, No. 14, pp. 6339-6343.
U.S. Appl. No. 17/090,176 Notice of Allowance dated Jun. 3, 2021.
U.S. Appl. No. 17/406,464 Notice of Allowance dated Dec. 9, 2021.
U.S. Appl. No. 17/090,176 Office Action dated Mar. 9, 2021.
Zakeri et al., Peak Height Pattern in Dichloro-Rhodamine and Energy Transfer Dye Terminator Sequencing, Biotechniques vol. 25 No. 3, pp. 406-414 (1998).
Brenner, et al. Gene expression analysis by massively parallel signature sequencing (MPSS) on microbead arrays. Nat Biotechnol. Jun. 2000;18(6):630-4.
Brenner, et al. In vitro cloning of complex mixtures of DNA on microbeads: physical separation of differentially expressed cDNAs. Proc Natl Acad Sci U S A. Feb. 15, 2000;97(4):1665-70.
Dressman, et al. Transforming single DNA molecules into fluorescent magnetic particles for detection and enumeration of genetic variations. Proc Natl Acad Sci USA. 2003;100(15):8817-8822.
Lizardi, et al. Mutation detection and single-molecule counting using isothermal rolling-circle amplification. Nature genetics vol. 19,3 (1998): 225-32.
Mitra, et al. Digital genotyping and haplotyping with polymerase colonies. Proceedings of the National Academy of Sciences of the United States of America vol. 100, 10 (2003): 5926-31.
Mitra, et al. Fluorescent in situ sequencing on polymerase colonies. Analytical biochemistry vol. 320,1 (2003): 55-65.
PCT/US2020/021909 International Search Report and Written Opinion dated Aug. 14, 2020.
PCT/US2021/049923 International Search Report and Written Opinion dated Feb. 14, 2022.
Reinartz, et al. Massively parallel signature sequencing (MPSS) as a tool for in-depth quantitative gene expression profiling in all organisms. Brief Funct Genomic Proteomic. Feb. 2002;1(1):95-104.
Tabor, S. et al. Effect of manganese ions on the incorporation of dideoxynucleotides by bacteriophage T7 DNA polymerase and *Escherichia coli* DNA polymerase I, Proc. Natl. Acad. Sci. USA. (1989) 86:4076-80.
U.S. Appl. No. 17/397,802 Non-Final Office Action dated Feb. 3, 2022.
Frazer et al., "Cross-Species Sequence Comparisons: A Review of Methods and Available Resources", Genome Research 2003, pp. 1-13.
Lathuiliere et al., "A Comprehensive Analysis of Deep Regression", In: Cornell University Library Computer Science Computer Vision and Pattern Recognition 2018, pp. 1-17.
Cohn et al., "Enhancer Identification using Transfer and Adversarial Deep Learning of DNA Sequences", In: bioRxiv 264200, Feb. 15, 2018, pp. 1-9.
Adessi et al., "Solid phase DNA amplification: characterisation of primer attachment and amplification mechanisms", Nucl. Acids Res, 2000, 28(20): E87, pp. 1-8.
Lederman, R., Homopolymer Length Filters. Technical Report. Yale University, Department of Computer Science, Oct. 25, 2012, pp. 1-12.
Au et al., "Improving PacBio Long Read Accuracy by Short Read Alighment", PLOS ONE, Oct. 2021, vol. 7, Issue 10, e46679, pp. 1-8.
Vineetha et al., "SPARK-MSNA: Efficient algorithm on Apache Spark for aligning multiple similar DNA/RNA sequences with supervised learning", Scientific reports vol. 9, 1 6631, Apr. 29, 2019, pp. 1-11.
Pemov et al., "DNA analysis with multiplex microarray-enhanced PCR", Nucleic Acids Research, vol. 33, No. 2, Oxford University Press 2005, pp. 1-9.

SEQUENCE LISTING

```
<160> NUMBER OF SEQ ID NOS: 28

<210> SEQ ID NO 1
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cgttataatg tggagagcat cgcgtcatcg gccttcaaaa aatacaagat attttttacct    60 ttggcataac acgacgtgag gcgagaccca ccggggggggg taccgaaaaa atgggggtgg   120
tcagcttga                                                           129

<210> SEQ ID NO 2
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tggagagcat cgcgtcatcg gccttcaaaa atacaagata ttttaccttt ggcataacac    60
gacgtgaggc gag                                                       73

<210> SEQ ID NO 3
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agagcatcgc gtcatcggcc ttcaaaaaat acaagatatt taccttttgg cataacacga    60
cgtgaggcga gacc                                                      74

<210> SEQ ID NO 4
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 4
ggccttcaaa atacaagata tttttacctt tggcataaca cgacgtgagg cgagacccac      60
cgggggggta cc                                                          72

<210> SEQ ID NO 5
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaaaatacaa gatatttacc tttggcataa cacgacgtga ggcgagaccc accgggggg       60 gtaccgaaaa atg                                                         73

<210> SEQ ID NO 6
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatattttta cctttggcat aacacgacgt gaggcgagac ccaccggggg ggtaccgaaa      60
aaatgggtgg tca                                                         73

<210> SEQ ID NO 7
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttttaccttt ggcataacac gacgtgaggc gagacccacc gggggtacc gaaaaaatgg       60 gggtggtcag cttg                                                        74

<210> SEQ ID NO 8
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
acacgacgtg aggcgagacc caccgggggg ggtaccgaaa aaatgggggt ggtcagcttg      60
accaaggatc gacata                                                      76

<210> SEQ ID NO 9
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
acccaccggg gggggtaccg aaaaatgggg tggtcagctt gaccaaggat cgacatacag     60
```
tctagggggt cact                                                           74

<210> SEQ ID NO 10
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 gggggggtacc gaaaaaatgg gggtggtcag cttgaccaag gatcgacata cagtctaggg      60
gtcactggac aggag                                                        75

<210> SEQ ID NO 11
<211> LENGTH: 173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
cgttataatg tggagagcat cgcgtcatcg gccttcaaaa aatacaagat atttttacct       60
ttggcataac acgacgtgag gcgagaccca ccgggggggg taccgaaaaa atggggggtgg     120 tcagcttgac caaggatcga catacagtct aggggggtcac tggacaggag agc             173

<210> SEQ ID NO 12
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
cgttataatg tggagagcat cgcgtcatcg gccttcaaat acaagatatt tacctttggc      60
ataacacgac gtgaggcgag acccaccggg taccgaaatg ggtggtcagc ttgaccaagg     120
atcgacatac agtctagggt cactggacag gagagc                                156

<210> SEQ ID NO 13
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tggagagcat cgcgtcatcg gccttcaaat acaagatatt tacctttggc ataacacgac      60
gtgaggcgag                                                              70

<210> SEQ ID NO 14
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agagcatcgc gtcatcggcc ttcaaataca agatatttac ctttggcata acacgacgtg      60
aggcgagacc                                                          70

<210> SEQ ID NO 15
<211> LENGTH: 65
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 15
ggccttcaaa tacaagatat ttacctttgg cataacacga cgtgaggcga gacccaccgg    60
gtacc                                                               65

<210> SEQ ID NO 16
<211> LENGTH: 64
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 16
aaatacaaga tatttacctt tggcataaca cgacgtgagg cgagacccac cgggtaccga    60
aatg                                                                64

<210> SEQ ID NO 17
<211> LENGTH: 64
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 17
gatatttacc tttggcataa cacgacgtga ggcgagaccc accgggtacc gaaatgggtg    60
gtca                                                                64

<210> SEQ ID NO 18
<211> LENGTH: 65
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 18
tttacctttg gcataacacg acgtgaggcg agacccaccg ggtaccgaaa tgggtggtca    60
gcttg                                                               65

<210> SEQ ID NO 19
<211> LENGTH: 66
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 19
acacgacgtg aggcgagacc caccgggtac cgaaatgggt ggtcagcttg accaaggatc    60
gacata                                                              66

<210> SEQ ID NO 20

```
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
acccaccggg taccgaaatg ggtggtcagc ttgaccaagg atcgacatac agtctagggt     60
cact                                                                  64

<210> SEQ ID NO 21
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gggtaccgaa atgggtggtc agcttgacca aggatcgaca tacagtctag ggtcactgga     60
caggag                                                                66

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgtctgttca gacgat                                                     16

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
catatgttca cacact                                                     16

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tatctgttca gtctct                                                     16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggtctgttca atacct                                                     16
```

```
<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
catgtgttca gacact                                                      16

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cgtctgttca cacata                                                      16

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tatctgttca gctagt                                                      16
```

METHODS AND SYSTEMS FOR SEQUENCE CALLING

CROSS-REFERENCE

This application is a continuation of U.S. patent application Ser. No. 17/406,464, filed Aug. 19, 2021, which is a continuation of U.S. patent application Ser. No. 17/090,176, filed Nov. 5, 2020, which is a continuation of U.S. patent application Ser. No. 16/845,278, filed Apr. 10, 2020, which is a continuation of International Patent Application No. PCT/US2018/057340, filed Oct. 24, 2018, which claims the benefit of U.S. Provisional Patent Application No. 62/577,450, filed Oct. 26, 2017, each of which applications is entirely incorporated herein by reference.

SEQUENCE LISTING

The instant application contains a Sequence Listing which has been submitted electronically in ASCII format and is hereby incorporated by reference in its entirety. Said ASCII copy, created on Jan. 18, 2021, is named 51024-705_304_SL.txt and is 8,795 bytes in size.

BACKGROUND

The goal to elucidate the entire human genome has created interest in technologies for rapid nucleic acid (e.g., DNA) sequencing, both for small and large scale applications. As knowledge of the genetic basis for human diseases increases, high-throughput DNA sequencing has been leveraged for myriad clinical applications. Despite the prevalence of nucleic acid sequencing methods and systems in a wide range of molecular biology and diagnostics applications, such methods and systems may encounter challenges in accurate base calling, such as when sequencing signals include regions of repeating nucleotide bases called homopolymers. In particular, sequencing methods that perform base calling based on quantified characteristic signals indicating nucleotide incorporation can have sequencing errors (e.g., in quantifying homopolymer lengths), stemming from random and unpredictable systematic variations in signal levels and context dependent signals that may be different for every sequence. Such signal variations and context dependency signals may cause issues with sequence (e.g., homopolymer) calling.

SUMMARY

Recognized herein is a need for improved base calling of sequences, such as sequences containing homopolymers. Methods and systems provided herein can significantly reduce or eliminate errors in quantifying homopolymer lengths and errors associated with context dependence. Such methods and systems may achieve accurate and efficient base calling of sequences (such as sequences containing homopolymers), quantification of homopolymer lengths, and quantification of context dependency in sequence signals.

In an aspect, disclosed herein is a method for sequencing a nucleic acid molecule, comprising: (a) sequencing said nucleic acid molecule to generate a plurality of sequence signals; and (b) determining base calls of said nucleic acid molecule based at least in part on (i) said plurality of sequence signals and (ii) quantified context dependency for at least a portion of said plurality of sequence signals. In some embodiments, said sequencing generates one or more imputed sequences, and said base calls of said nucleic acid molecule are determined based at least in part on (i) said one or more imputed sequences, and (ii) quantified context dependency for at least a portion of said one or more imputed sequences. In some embodiments, (b) is performed in real time with said sequencing of (a). In some embodiments, said one or more imputed sequences comprise one or more homopolymers of length N. In some embodiments, N is at least 1 base, at least 2 bases, or at least 3 bases. In some embodiments, prior to (b), said plurality of sequence signals are pre-processed to remove systematic errors. In some embodiments, the method further comprises, prior to (b), pre-processing said plurality of sequence signals to remove systematic error(s). In some embodiments, the method further comprises determining lengths of said homopolymers based at least on clustering of said homopolymers or associated signals.

In some embodiments, said plurality of sequence signals is generated by sequencing nucleic acids of a subject. In some embodiments, said plurality of sequence signals is generated by massively parallel array sequencing. In some embodiments, said plurality of sequence signals is generated by flow sequencing.

In another aspect, disclosed herein is a method for quantifying context dependency of a plurality of sequence signals, comprising: (a) sequencing deoxyribonucleic acid (DNA) molecule(s) to provide a plurality of sequence signals and one or more imputed sequences, wherein said DNA molecule(s) comprise a known sequence; and (b) for a given locus of a plurality of loci, determining one or more expected signals for said given locus based at least on (i) said plurality of sequence signals and/or said one or more imputed sequences, and (ii) said known sequence. In some embodiments, the method further comprises: (c) sequencing a second set of DNA molecules comprising unknown sequences, thereby generating a second plurality of sequence signals; and (d) determining base calls of said second set of DNA molecules based at least in part on (i) said second plurality of sequence signals, and (ii) at least a portion of said one or more expected signals. In some embodiments, sequencing said second set of DNA molecules generates one or more imputed sequences, and said base calls of said second set of DNA molecules are determined based at least in part on said one or more imputed sequences.

In some embodiments, said DNA molecules comprise synthetic templates. In some embodiments, said known sequence comprises one or more homopolymers of length N. In some embodiments, N is at least 1 base, at least 2 bases, or at least 3 bases. In some embodiments, said one or more imputed sequences comprise one or more homopolymers of length N. In some embodiments, N is at least 1 base, at least 2 bases, or at least 3 bases. In some embodiments, quantifying said context dependency comprises establishing a context specific mapping between signal amplitudes and known sequences for each of a plurality of loci. In some embodiments, said context dependency is quantified based on a distribution of said sequence signals or of homopolymer lengths of said imputed sequences. In some embodiments, prior to (b), said plurality of sequence signals are pre-processed to remove systematic errors. In some embodiments, the method further comprises, prior to (b), pre-processing said plurality of sequence signals to remove systematic error(s). In some embodiments, the method further comprises determining lengths of said homopolymers based at least on clustering of said homopolymers or associated signals.

In some embodiments, said plurality of sequence signals is generated by sequencing nucleic acids of a subject. In some embodiments, said plurality of sequence signals is generated by massively parallel array sequencing. In some embodiments, said plurality of sequence signals is generated by flow sequencing. In some embodiments, said base calls are determined based at least on a context dependency of said second plurality of sequence signals. In some embodiments, said base calls are determined based at least on a context dependency of said second plurality of sequence signals and said one or more imputed sequences. In some embodiments, (d) is performed in real time with said sequencing of (c).

In another aspect, disclosed herein is a method for processing a plurality of sequence signals, comprising: (a) sequencing a nucleic acid sample to provide a plurality of sequence signals and imputed sequences; (b) truncating each identified imputed homopolymer sequence of at least N bases of said plurality of imputed sequences to a homopolymer sequence of bases of length N, to yield one or more HpN truncated sequences; (c) aligning said one or more HpN truncated sequences to a truncated reference(s), which truncated reference(s) has been HpN truncated and thereby comprises one or more homopolymer sequences truncated to said length N; and (d) generating a consensus sequence from said one or more HpN truncated sequences aligned to said HpN truncated reference(s), which consensus sequence comprises a homopolymer sequence of said length N, based at least on said one or more HpN truncated sequences aligned to said HpN truncated reference(s) and/or sequence signals associated with said one or more HpN truncated sequences aligned to said HpN truncated reference(s).

In some embodiments, N is 5 bases. In some embodiments, N is 6 bases. In some embodiments, N is 7 bases. In some embodiments, N is 8 bases. In some embodiments, a length estimation error of said homopolymer sequence is calculated based at least on a distribution of signals or imputed homopolymer lengths of said one or more HpN truncated sequences aligned to said HpN truncated reference(s). In some embodiments, prior to (b), said plurality of sequence signals are pre-processed to remove systematic error(s). In some embodiments, the method further comprises, prior to (b), pre-processing said plurality of sequence signals to remove systematic error(s). In some embodiments, the method further comprises determining lengths of said homopolymer sequences based at least on clustering of said homopolymer sequences or associated signals.

In some embodiments, said plurality of sequence signals is generated by sequencing nucleic acids of a subject, and said HpN truncated reference(s) comprises an HpN truncated reference genome of a species of said subject. In some embodiments, a number of lengths computed or classified in (d) is restricted based at least on the ploidy of said species of said subject. In some embodiments, said plurality of sequence signals and imputed sequences is generated by massively parallel array sequencing. In some embodiments, said plurality of sequence signals and imputed sequences is generated by flow sequencing.

In another aspect, disclosed herein is a method for quantifying context dependency of a plurality of sequence signals and imputed sequences, the method comprising: (a) sequencing deoxyribonucleic acid (DNA) molecule(s) to provide a plurality of sequence signals and imputed sequences, wherein said DNA molecule(s) comprise a known sequence; (b) truncating each identified imputed homopolymer sequence of at least N bases of said plurality of imputed sequences to a homopolymer sequence of bases of length N, to yield one or more HpN truncated sequences; (c) aligning said one or more HpN truncated sequences to a truncated reference(s), which truncated reference(s) has been HpN truncated and thereby comprises one or more homopolymer sequences HpN truncated to said length N; and (d) quantifying said context dependency of associated sequence signals based at least on (i) said one or more HpN truncated sequences aligned to said HpN truncated reference(s) and/or sequence signals associated with said one or more HpN truncated sequences aligned to said HpN truncated reference(s), and (ii) said known sequence. In some embodiments, the method further comprises: (e) sequencing a second set of DNA molecules comprising unknown sequences, thereby generating a second plurality of sequence signals and imputed sequences; (f) truncating each identified imputed second homopolymer sequence of at least N bases of said second plurality of imputed sequences to a homopolymer sequence of bases of length N, to yield one or more second HpN truncated sequences; (g) aligning said one or more second HpN truncated sequences to said HpN truncated reference(s); and (h) determining homopolymer lengths of said second plurality of DNA molecules based at least on (i) said one or more HpN truncated sequences aligned to said HpN truncated reference(s) and/or sequence signals associated with said one or more HpN truncated sequences aligned to said HpN truncated reference(s) and (ii) said quantified context dependency.

In some embodiments, said quantified context dependency is classified for a given context. In some embodiments, said given context is an n-base context, wherein 'n' is a number greater than or equal to 5. In some embodiments, said DNA molecule(s) is derived from a ribonucleic acid (RNA) molecule(s). In some embodiments, said plurality of sequence signals and imputed sequences is generated by massively parallel array sequencing. In some embodiments, said plurality of sequence signals and imputed sequences is generated by flow sequencing. In some embodiments, quantifying said context dependency comprises establishing a context specific mapping between signal amplitudes and homopolymer length for each of a plurality of loci.

In another aspect, disclosed herein is a method for quantifying context dependency of a plurality of sequence signals and imputed sequences, the method comprising: (a) sequencing deoxyribonucleic acid (DNA) molecule(s) to provide a plurality of sequence signals and imputed sequences, wherein said DNA molecule(s) comprise a known sequence; (b) truncating each identified imputed homopolymer sequence of at least N bases of said plurality of imputed sequences to a homopolymer sequence of bases of length N, to yield one or more HpN truncated sequences; (c) aligning said one or more HpN truncated sequences to a truncated reference(s), which truncated reference(s) has been HpN truncated and thereby comprises one or more homopolymer sequences truncated to said length N; and (d) for each of a plurality of loci in said HpN truncated reference(s), determining an expected signal for said locus based at least on (i) said one or more HpN truncated sequences aligned to said HpN truncated reference(s) and/or sequence signals associated with said one or more HpN truncated sequences aligned to said HpN truncated reference(s), and (ii) said known sequence. In some embodiments, the method further comprises: (e) sequencing a second set of DNA molecules comprising unknown sequences, thereby generating a second plurality of sequence signals and imputed sequences; (f) truncating each identified imputed second homopolymer sequence of at least N bases of said second plurality of imputed sequences to a homopolymer sequence of bases of length N, to yield one or more second HpN truncated sequences; (g) aligning said one or more second HpN truncated sequences to said HpN truncated reference(s); and (h) determining homopolymer lengths of said second set of DNA molecules based at least on (i) said one or more HpN truncated sequences aligned to said HpN truncated reference(s) and/or sequence signals associated with said one or more HpN truncated sequences aligned to said HpN truncated reference(s) and (ii) said known sequence.

In some embodiments, said DNA molecule(s) is derived from a ribonucleic acid molecule(s). In some embodiments, said plurality of sequence signals and imputed sequences is generated by massively parallel array sequencing. In some embodiments, said plurality of sequence signals and imputed sequences is generated by flow sequencing. In some embodiments, quantifying said context dependency comprises establishing a context specific mapping between signal amplitudes and homopolymer length for each of a plurality of loci.

In another aspect, disclosed herein is a method for processing a plurality of sequence signals, comprising: (a) sequencing a nucleic acid sample to provide a plurality of sequence signals and imputed sequences; (b) processing said plurality of sequence signals and imputed sequences to determine a set of one or more sequences comprising homopolymer sequences; (c) processing said plurality of sequence signals and imputed sequences to identify a presence and an estimated length of at least a portion of said homopolymer sequences; and (d) refining said estimated lengths using secondary assay data. In some embodiments, said plurality of sequence signals and imputed sequences is generated by massively parallel array sequencing. In some embodiments, said plurality of sequence signals and imputed sequences is generated by flow sequencing.

In another aspect, disclosed herein is a method for processing a plurality of sequence signals, comprising: (a) sequencing a nucleic acid sample to provide said plurality of sequence signals; (b) aligning said plurality of sequence signals to a reference signal; (c) identifying a reference locus comprising a homopolymer sequence based at least on said aligned sequence signals; and (d) generating a consensus sequence from said plurality of sequence signals aligned to said reference signal, which consensus sequence comprises a homopolymer sequence of N bases, based at least on said identified reference locus, a length of said homopolymer sequence of said reference locus, and said reference signal.

In some embodiments, a length estimation error of said homopolymer sequence is calculated based at least on a distribution of signals or imputed homopolymer lengths of said plurality of sequence signals aligned to said reference signal. In some embodiments, prior to (b), said plurality of sequence signals is pre-processed to remove systematic error(s). In some embodiments, the method further comprises, prior to (b), pre-processing said plurality of sequence signals to remove systematic error(s). In some embodiments, said plurality of sequence signals is generated by sequencing nucleic acids of a subject, and said reference signal comprises a reference genome of a species of said subject. In some embodiments, a number of lengths computed or classified is restricted based at least on the ploidy of said species of said subject. In some embodiments, said plurality of sequence signals is generated by massively parallel array sequencing. In some embodiments, said plurality of sequence signals is generated by flow sequencing.

In another aspect, disclosed herein is a method for quantifying context dependency of a plurality of sequence signals, the method comprising: (a) sequencing deoxyribonucleic acid (DNA) molecule(s) to provide a plurality of sequence signals, wherein said DNA molecule(s) comprise a known sequence; (b) aligning said plurality of sequence signals to a reference signal; and (c) quantifying said context dependency in said plurality of sequence signals aligned to said reference signal, based at least on said known sequence. In some embodiments, said aligning comprises analog signal processing. In some embodiments, the method further comprises: (d) sequencing a second set of DNA molecules comprising unknown sequences, thereby generating a second plurality of sequence signals; (e) aligning said second plurality of sequence signals to said reference signal; and (f) determining homopolymer lengths of said second set of DNA molecules based at least on said plurality of sequence signals aligned to said reference signal and said quantified context dependency.

In some embodiments, said DNA molecule(s) is derived from a ribonucleic acid molecule(s). In some embodiments, said plurality of sequence signals is generated by massively parallel array sequencing. In some embodiments, said plurality of sequence signals is generated by flow sequencing. In some embodiments, quantifying said context dependency comprises establishing a context specific mapping between signal amplitudes and homopolymer length for each of a plurality of loci.

In another aspect, disclosed herein is a method for quantifying context dependency of a plurality of sequence signals, the method comprising: (a) sequencing deoxyribonucleic acid (DNA) molecule(s) to provide said plurality of sequence signals, wherein said DNA molecule(s) comprise a known sequence; (b) aligning said plurality of sequence signals to a reference signal; and (c) for each of a plurality of loci in said reference signal, determining an expected signal for said locus based at least on said plurality of sequence signals aligned to said reference signal and said known sequence. In some embodiments, said aligning comprises analog signal processing. In some embodiments, the method further comprises: (d) sequencing a second set of DNA molecules comprising unknown sequences, thereby generating a second plurality of sequence signals; (e) aligning said second plurality of sequence signals to said reference signal; and (f) determining homopolymer lengths of said second set of DNA molecules based at least on said plurality of sequence signals aligned to said reference signal and said known sequence.

In some embodiments, said DNA molecule(s) is derived from a ribonucleic acid molecule(s). In some embodiments, said plurality of sequence signals is generated by massively parallel array sequencing. In some embodiments, said plurality of sequence signals is generated by flow sequencing.

In another aspect, disclosed herein is a method for processing a plurality of sequence signals, comprising: (a) sequencing a nucleic acid sample to provide said plurality of sequence signals; (b) aligning said plurality of sequence signals to a reference signal; (c) identifying a genomic locus comprising a homopolymer sequence based at least on said aligned sequence signals; (d) processing said plurality of sequence signals aligned to said reference signal to identify a presence and an estimated length of said homopolymer sequence; and (e) refining said estimated length using secondary assay data. In some embodiments, said aligning comprises analog signal processing. In some embodiments, said plurality of sequence signals is generated by massively parallel array sequencing. In some embodiments, said plurality of sequence signals is generated by flow sequencing.

In another aspect, disclosed herein is a system for sequencing a nucleic acid molecule, comprising: a database that stores a plurality of sequence signals generated upon sequencing said nucleic acid molecule; and one or more computer processors operatively coupled to said database, wherein said one or more computer processors are individual or collectively programmed to determine base calls of said nucleic acid molecule based at least in part on (i) said plurality of sequence signals and (ii) quantified context dependency for at least a portion of said plurality of sequence signals.

In another aspect, disclosed herein is a system for processing a plurality of sequence signals, comprising: a database that stores said plurality of sequence signals and a context dependency corresponding to said plurality of sequence signals; and one or more computer processors coupled to said database, wherein said one or more computer processors are individually or collectively programmed to: for each of a plurality of loci, determine an expected signal for said locus based at least on (i) said plurality of sequence signals and/or a plurality of imputed sequences corresponding to said plurality of sequence signals, and (ii) a known sequence. In some embodiments, said context dependency comprises a context specific mapping between signal amplitudes and known sequences for each of a plurality of loci.

In another aspect, disclosed herein is a system for processing a plurality of sequence signals and imputed sequences, comprising: a database that stores said plurality of sequence signals and imputed sequences; and one or more computer processors coupled to said database, wherein said one or more computer processors are individually or collectively programmed to: (a) truncate each identified imputed homopolymer sequence of at least N bases of said plurality of imputed sequences to a homopolymer sequence of bases of length N, to yield one or more HpN truncated sequences; (b) align said one or more HpN truncated sequences to a truncated reference(s), which truncated reference(s) has been HpN truncated and thereby comprises one or more homopolymer sequences truncated to said length N; and (c) generate a consensus sequence from said one or more HpN truncated sequences aligned to said HpN truncated reference(s), which consensus sequence comprises a homopolymer sequence of said length N, based at least on said one or more HpN truncated sequences aligned to said reference(s) and/or sequence signals associated with said one or more HpN truncated sequences aligned to said HpN truncated reference(s).

In another aspect, disclosed herein is a system for quantifying context dependency of a plurality of sequence signals and imputed sequences, comprising: a database that stores said plurality of sequence signals and imputed sequences; and one or more computer processors coupled to said database, wherein said one or more computer processors are individually or collectively programmed to: (a) truncate each identified imputed homopolymer sequence of at least N bases of said plurality of imputed sequences to a homopolymer sequence of bases of length N, to yield one or more HpN truncated sequences; (b) align said one or more HpN truncated sequences to a truncated reference(s), which truncated reference(s) has been HpN truncated and thereby comprises one or more homopolymer sequences truncated to said length N; and (c) quantify said context dependency of associated sequence signals based at least on (i) said one or more HpN truncated sequences aligned to said HpN truncated reference(s) and/or sequence signals associated with said one or more HpN truncated sequences aligned to said HpN truncated reference(s), and (ii) said known sequence. In some embodiments, said database stores training data, which training data comprises reference-aligned signals or context dependencies quantified from reference-aligned signals.

In another aspect, disclosed herein is a system for quantifying context dependency of a plurality of sequence signals and imputed sequences, comprising: a database that stores said plurality of sequence signals and imputed sequences; and one or more computer processors coupled to said database, wherein said one or more computer processors are individually or collectively programmed to: (a) truncate each identified imputed homopolymer sequence of at least N bases of said plurality of imputed sequences to a homopolymer sequence of bases of length N, to yield one or more HpN truncated sequences; (b) align said one or more HpN truncated sequences to a truncated reference(s), which truncated reference(s) has been HpN truncated and thereby comprises one or more homopolymer sequences truncated to said length N; and (c) for each of a plurality of loci in said HpN truncated reference(s), determine an expected signal for said locus based at least on (i) said one or more HpN truncated sequences aligned to said HpN truncated reference(s) and/or sequence signals associated with said one or more HpN truncated sequences aligned to said HpN truncated reference(s), and (ii) said known sequence.

In another aspect, disclosed herein is a system for processing a plurality of sequence signals and imputed sequences, comprising: a database that stores said plurality of sequence signals and imputed sequences; and one or more computer processors coupled to said database, wherein said one or more computer processors are individually or collectively programmed to: (a) process said plurality of sequence signals and imputed sequences to determine a set of one or more sequences comprising homopolymer sequences; (b) process said plurality of sequence signals and imputed sequences to identify a presence and an estimated length of at least a portion of said homopolymer sequences; and (c) refine said estimated lengths using secondary assay data.

In another aspect, disclosed herein is a system for processing a plurality of sequence signals, comprising: a database that stores said plurality of sequence signals; and one or more computer processors coupled to said database, wherein said one or more computer processors are individually or collectively programmed to: (a) align said plurality of sequence signals to a reference signal; (b) identify a reference locus comprising a homopolymer sequence based at least on said aligned sequence signals; and (c) generate a consensus sequence from said plurality of sequence signals aligned to said reference signal, which consensus sequence comprises a homopolymer sequence of N bases, based at least on said identified reference locus, a length of said homopolymer sequence of said reference locus, and said reference signal.

In another aspect, disclosed herein is a system for quantifying context dependency of a plurality of sequence signals, comprising: a database that stores said plurality of sequence signals; and one or more computer processors coupled to said database, wherein said one or more computer processors are individually or collectively programmed to: (a) align said plurality of sequence signals to a reference signal; and (b) quantify said context dependency in said plurality of sequence read signals aligned to said reference signal, based at least on a known sequence associated with said plurality of sequence signals.

In another aspect, disclosed herein is a system for quantifying context dependency of a plurality of sequence signals, comprising: a database that stores said plurality of sequence signals; and one or more computer processors coupled to said database, wherein said one or more computer processors are individually or collectively programmed to: (a) align said plurality of sequence signals to a reference signal; and (b) for each of a plurality of loci in said reference signal, determine an expected signal for said locus based at least on said plurality of sequence signals aligned to said reference signal and a known sequence associated with said plurality of sequence signals.

In another aspect, disclosed herein is a system for processing a plurality of sequence signals, comprising: a database that stores said plurality of sequence signals; and one or more computer processors coupled to said database, wherein said one or more computer processors are individually or collectively programmed to: (a) align said plurality of sequence signals to a reference signal; (b) identify a genomic locus comprising a homopolymer sequence based at least on said aligned sequence signals; (c) process said plurality of sequence signals aligned to said reference signal to identify a presence and an estimated length of said homopolymer sequence; and (d) refine said estimated length using secondary assay data.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 3 discloses SEQ ID NOS 1-21, respectively, in order of appearance.

FIG. 4 discloses SEQ ID NOS 22-28, respectively, in order of appearance.

FIG. 5 discloses SEQ ID NOS 22-28, respectively, in order of appearance.

DETAILED DESCRIPTION

Figure 1:
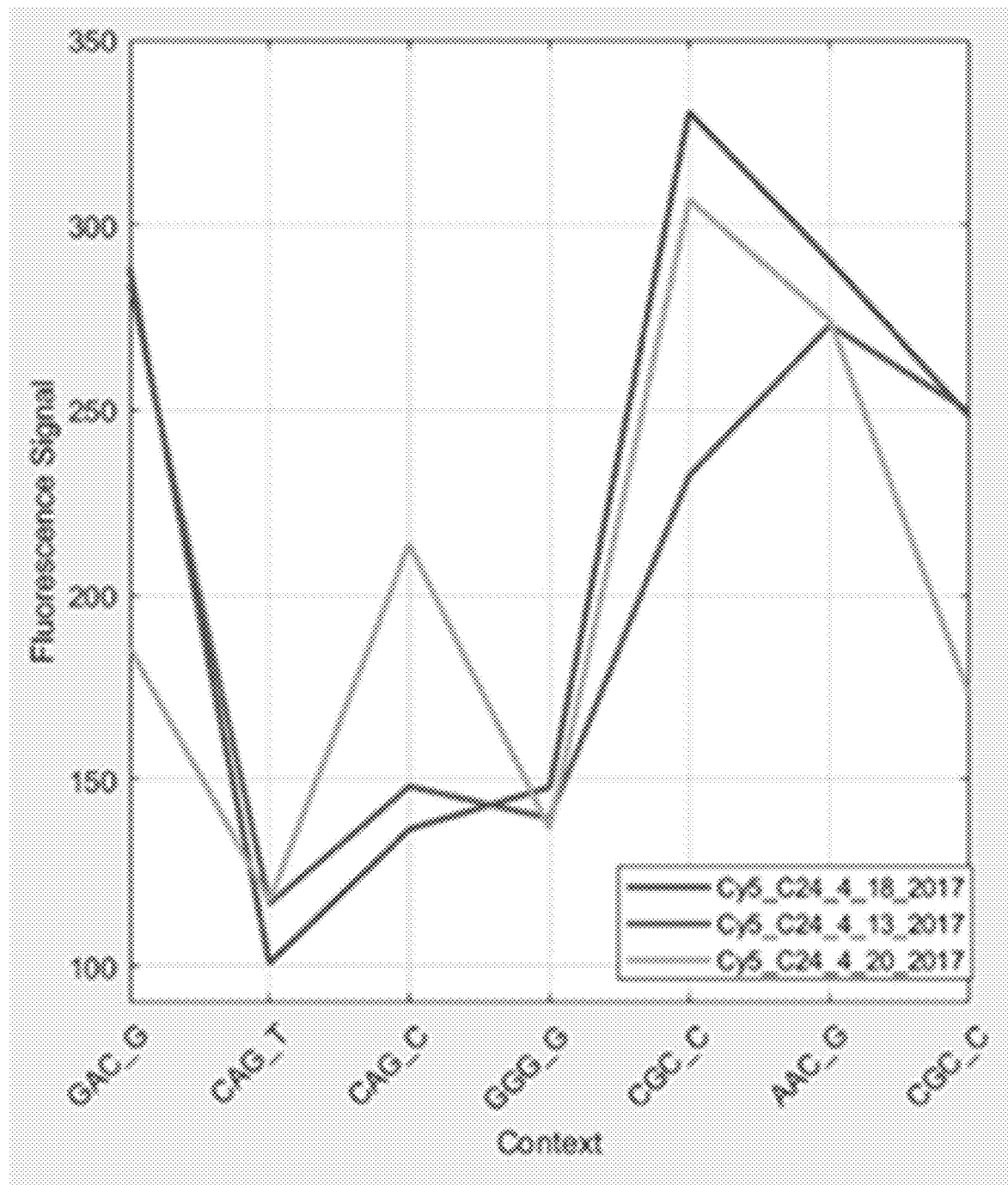
FIG. 1 shows an example of reproducible fluorescent signal variations for 6 local contexts for a Cy5-labeled nucleotide analog.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "sequencing," as used herein, generally refers to a process for generating or identifying a sequence of a biological molecule, such as a nucleic acid molecule. Such sequence may be a nucleic acid sequence, which may include a sequence of nucleic acid bases. Sequencing methods may be massively parallel array sequencing (e.g., Illumina sequencing), which may be performed using template nucleic acid molecules immobilized on a support, such as a flow cell or beads. Sequencing methods may include, but are not limited to: high-throughput sequencing, next-generation sequencing, sequencing-by-synthesis, flow sequencing, massively-parallel sequencing, shotgun sequencing, single-molecule sequencing, nanopore sequencing, pyrosequencing, semiconductor sequencing, sequencing-by-ligation, sequencing-by-hybridization, RNA-Seq (Illumina), Digital Gene Expression (Helicos), Single Molecule Sequencing by Synthesis (SMSS) (Helicos), Clonal Single Molecule Array (Solexa), and Maxim-Gilbert sequencing.

The term "flow sequencing," as used herein, generally refers to a sequencing-by-synthesis (SBS) process in which cyclic or acyclic introduction of single nucleotide solutions produce discrete DNA extensions that are sensed (e.g., by a detector that detects fluorescence signals from the DNA extensions).

The term "subject," as used herein, generally refers to an individual having a biological sample that is undergoing processing or analysis. A subject can be an animal or plant. The subject can be a mammal, such as a human, dog, cat, horse, pig, or rodent. The subject can have or be suspected of having a disease, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. The subject can have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease.

The term "sample," as used herein, generally refers to a biological sample. Examples of biological samples include nucleic acid molecules, amino acids, polypeptides, proteins, carbohydrates, fats, or viruses. In an example, a biological sample is a nucleic acid sample including one or more nucleic acid molecules, such as deoxyribonucleic acid (DNA) and/or ribonucleic acid (RNA). The nucleic acid molecules may be cell-free or cell-free nucleic acid molecules, such as cell free DNA or cell free RNA. The nucleic acid molecules may be derived from a variety of sources including human, mammal, non-human mammal, ape, monkey, chimpanzee, reptilian, amphibian, or avian, sources. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like. Cell free polynucleotides may be fetal in origin (via fluid taken from a pregnant subject), or may be derived from tissue of the subject itself.

The term "nucleic acid," or "polynucleotide," as used herein, generally refers to a molecule comprising one or more nucleic acid subunits, or nucleotides. A nucleic acid may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups.

Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate (dNTP), which can be selected from deoxyadenosine triphosphate (dATP), deoxycytidine triphosphate (dCTP), deoxyguanosine triphosphate (dGTP), uridine triphosphate (dUTP) and deoxythymidine triphosphate (dTTP) dNTPs, that include detectable tags, such as luminescent tags or markers (e.g., fluorophores). A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double-stranded. In some cases, a nucleic acid molecule is circular.

The terms "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or ribonucleotides (RNA), or analogs thereof. A nucleic acid molecule can have a length of at least about 10 bases, 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bio informatics applications such as functional genomics and homology searching. Oligonucleotides may include one or more nonstandard nucleotide(s), nucleotide analog(s), and/or modified nucleotides.

The term "nucleotide analogs," as used herein, may include, but are not limited to, diaminopurine, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl) uracil, (acp3)w, 2,6-diaminopurine, phosphoroselenoate nucleic acids, and the like. In some cases, nucleotides may include modifications in their phosphate moieties, including modifications to a triphosphate moiety. Additional, non-limiting examples of modifications include phosphate chains of greater length (e.g., a phosphate chain having 4, 5, 6, 7, 8, 9, 10, or more than 10 phosphate moieties), modifications with thiol moieties (e.g., alpha-thio triphosphate and beta-thiotriphosphates) or modifications with selenium moieties (e.g., phosphoroselenoate nucleic acids). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic millimeter (mm), higher safety (e.g., resistance to accidental or purposeful synthesis of natural toxins), easier discrimination in photo-programmed polymerases, or lower secondary structure. Nucleotide analogs may be capable of reacting or bonding with detectable moieties for nucleotide detection.

The term "free nucleotide analog" as used herein, generally refers to a nucleotide analog that is not coupled to an additional nucleotide or nucleotide analog. Free nucleotide analogs may be incorporated in to the growing nucleic acid chain by primer extension reactions.

As used herein, the term "primer(s)" generally refers to a polynucleotide which is complementary to the template nucleic acid. The complementarity or homology or sequence identity between the primer and the template nucleic acid may be limited. The length of the primer may be between 8 nucleotide bases to 50 nucleotide bases. The length of the primer may be greater than or equal to 6 nucleotide bases, 7 nucleotide bases, 8 nucleotide bases, 9 nucleotide bases, 10 nucleotide bases, 11 nucleotide bases, 12 nucleotide bases, 13 nucleotide bases, 14 nucleotide bases, 15 nucleotide bases, 16 nucleotide bases, 17 nucleotide bases, 18 nucleotide bases, 19 nucleotide bases, 20 nucleotide bases, 21 nucleotide bases, 22 nucleotide bases, 23 nucleotide bases, 24 nucleotide bases, 25 nucleotide bases, 26 nucleotide bases, 27 nucleotide bases, 28 nucleotide bases, 29 nucleotide bases, 30 nucleotide bases, 31 nucleotide bases, 32 nucleotide bases, 33 nucleotide bases, 34 nucleotide bases, 35 nucleotide bases, 37 nucleotide bases, 40 nucleotide bases, 42 nucleotide bases, 45 nucleotide bases, 47 nucleotide bases, or 50 nucleotide bases.

A primer may exhibit sequence identity or homology or complementarity to the template nucleic acid. The homology or sequence identity or complementarity between the primer and a template nucleic acid may be based on the length of the primer. For example, if the primer length is about 20 nucleic acids, it may contain 10 or more contiguous nucleic acid bases complementary to the template nucleic acid.

The term "primer extension reaction," as used herein, generally refers to the binding of a primer to a strand of the template nucleic acid, followed by elongation of the primer(s). It may also include, denaturing of a double-stranded nucleic acid and the binding of a primer strand to either one or both of the denatured template nucleic acid strands, followed by elongation of the primer(s). Primer extension reactions may be used to incorporate nucleotides or nucleotide analogs to a primer in template-directed fashion by using enzymes (polymerizing enzymes).

The term "polymerase," as used herein, generally refers to any enzyme capable of catalyzing a polymerization reaction. Examples of polymerases include, without limitation, a nucleic acid polymerase. The polymerase can be naturally occurring or synthesized. In some cases, a polymerase has relatively high processivity. An example polymerase is a Φ29 polymerase or a derivative thereof. A polymerase can be a polymerization enzyme. In some cases, a transcriptase or a ligase is used (i.e., enzymes which catalyze the formation of a bond). Examples of polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some cases, the polymerase is a single subunit polymerase. The polymerase can have high processivity, namely the capability of the polymerase to consecutively incorporate nucleotides into a nucleic acid template without releasing the nucleic acid template. In some cases, a polymerase is a polymerase modified to accept dideoxynucleotide triphosphates, such as for example, Taq polymerase having a 667Y mutation (see e.g., Tabor et al, PNAS, 1995, 92, 6339-6343, which is herein incorporated by reference in its entirety for all purposes). In some cases, a polymerase is a polymerase having a modified nucleotide binding, which may be useful for nucleic acid sequencing, with non-limiting examples that include ThermoSequenas polymerase (GE Life Sciences), AmpliTaq FS (ThermoFisher) polymerase and Sequencing Pol polymerase (Jena Bioscience). In some cases, the polymerase is genetically engineered to have discrimination against dideoxynucleotides, such, as for example, Sequenase DNA polymerase (ThermoFisher).

The term "support," as used herein, generally refers to a solid support such as a slide, a bead, a resin, a chip, an array, a matrix, a membrane, a nanopore, or a gel. The solid support may, for example, be a bead on a flat substrate (such as glass, plastic, silicon, etc.) or a bead within a well of a substrate. The substrate may have surface properties, such as textures, patterns, microstructure coatings, surfactants, or any combination thereof to retain the bead at a desire location (such as in a position to be in operative communication with a detector). The detector of bead-based supports may be configured to maintain substantially the same read rate independent of the size of the bead. The support may be a flow cell or an open substrate. Furthermore, the support may comprise a biological support, a non-biological support, an organic support, an inorganic support, or any combination thereof. The support may be in optical communication with the detector, may be physically in contact with the detector, may be separated from the detector by a distance, or any combination thereof. The support may have a plurality of independently addressable locations. The nucleic acid molecules may be immobilized to the support at a given independently addressable location of the plurality of independently addressable locations. Immobilization of each of the plurality of nucleic acid molecules to the support may be aided by the use of an adaptor. The support may be optically coupled to the detector. Immobilization on the support may be aided by an adaptor.

The term "label," as used herein, generally refers to a moiety that is capable of coupling with a species, such as, for example, a nucleotide analog. In some cases, a label may be a detectable label that emits a signal (or reduces an already emitted signal) that can be detected. In some cases, such a signal may be indicative of incorporation of one or more nucleotides or nucleotide analogs. In some cases, a label may be coupled to a nucleotide or nucleotide analog, which nucleotide or nucleotide analog may be used in a primer extension reaction. In some cases, the label may be coupled to a nucleotide analog after the primer extension reaction. The label, in some cases, may be reactive specifically with a nucleotide or nucleotide analog. Coupling may be covalent or non-covalent (e.g., via ionic interactions, Van der Waals forces, etc.). In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl)phosphine (TCEP)) or enzymatically cleavable (e.g., via an esterase, lipase, peptidase, or protease).

In some cases, the label may be optically active. In some embodiments, an optically-active label is an optically-active dye (e.g., fluorescent dye). Non-limiting examples of dyes include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxy-pyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores.

In some examples, labels may be nucleic acid intercalator dyes. Examples include, but are not limited to ethidium bromide, YOYO-1, SYBR Green, and EvaGreen. The near-field interactions between energy donors and energy acceptors, between intercalators and energy donors, or between intercalators and energy acceptors can result in the generation of unique signals or a change in the signal amplitude. For example, such interactions can result in quenching (i.e., energy transfer from donor to acceptor that results in non-radiative energy decay) or Forster resonance energy transfer (FRET) (i.e., energy transfer from the donor to an acceptor that results in radiative energy decay). Other examples of labels include electrochemical labels, electrostatic labels, colorimetric labels and mass tags.

The term "quencher," as used herein, generally refers to molecules that can reduce an emitted signal. Labels may be quencher molecules. For example, a template nucleic acid molecule may be designed to emit a detectable signal. Incorporation of a nucleotide or nucleotide analog comprising a quencher can reduce or eliminate the signal, which reduction or elimination is then detected. In some cases, as described elsewhere herein, labeling with a quencher can occur after nucleotide or nucleotide analog incorporation. Examples of quenchers include Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare). Examples of donor molecules whose signals can be reduced or eliminated in conjunction with the above quenchers include fluorophores such as Cy3B, Cy3, or Cy5; Dy-Quenchers (Dyomics), such as DYQ-660 and DYQ-661; fluorescein-5-maleimide; 7-diethyl amino-3-(4'-maleimidylphenyl)-4-methylcoumarin (CPM); N-(7-dimethyl amino-4-methylcoumarin-3-yl) maleimide (DACM) and ATTO fluorescent quenchers (ATTO-TEC GmbH), such as ATTO 540Q, 580Q, 612Q, 647N, Atto-633-iodoacetamide, tetramethylrhodamine iodoacetamide or Atto-488 iodoacetamide. In some cases, the label may be a type that does not self-quench for example, Bimane derivatives such as Monobromobimane.

The term "detector," as used herein, generally refers to a device that is capable of detecting a signal, including a signal indicative of the presence or absence of an incorporated nucleotide or nucleotide analog. In some cases, a detector can include optical and/or electronic components that can detect signals. The term "detector" may be used in detection methods. Non-limiting examples of detection methods include optical detection, spectroscopic detection, electrostatic detection, electrochemical detection, and the like. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

The terms "signal," "signal sequence," and "sequence signal," as used herein, generally refer to a series of signals (e.g., fluorescence measurements) associated with a DNA molecule or clonal population of DNA, comprising primary data. Such signals may be obtained using a high-throughput sequencing technology (e.g., flow SBS). Such signals may be processed to obtain imputed sequences (e.g., during primary analysis).

The terms "sequence" or "sequence read," as used herein, generally refer to a series of nucleotide assignments (e.g, by base calling) made during a sequencing process. Such sequences may be derived from signal sequences (e.g., during primary analysis).

The term "homopolymer," as used herein, generally refers to a sequence of 0, 1, 2, . . . , N sequential nucleotides. For example, a homopolymer containing sequential A nucleotides may be represented as A, AA, AAA, . . . , up to N sequential A nucleotides.

The term "HpN truncation," as used herein, generally refers to a method of processing a set of one or more sequences such that each homopolymer of the set of one or more sequences having a length greater than or equal to an integer N is truncated to a homopolymer of length N. For example, HpN truncation of the sequence "AGGGGGT" to 3 bases may result in a truncated sequence of "AGGGT."

The term "analog alignment," as used herein, generally refers to alignment of signal sequences to a reference signal sequence.

The term "context dependence" or "context dependency," as used herein, generally refers to signal correlations with local sequence, relative nucleotide representation, or genomic locus. Signals for a given sequence may vary due to context dependency, which may depend on the local sequence, relative nucleotide representation of the sequence, or genomic locus of the sequence.

Local Context Quantification for Base Calling

Flow sequencing by synthesis (SBS) typically comprises performing repeated DNA extension cycles, wherein individual species of nucleotides and/or labeled analogs are presented to a primer-template-polymerase complex, which then incorporates the nucleotide if complementary. The product of each flow may be measured for each clonal population of templates, e.g., a bead or a colony. The resulting nucleotide incorporations may be detected and quantified by unambiguously distinguishing signals corresponding to or associated with zero, one, two, three, four, five, six, seven, eight, nine, ten, or more than ten sequential incorporations. Accurate quantification of such multiple sequential incorporations comprises quantifying characteristic signals for each possible homopolymer of 0, 1, 2, . . . , N sequential nucleotides incorporated on a colony in each flow. For example, a homopolymer containing sequential A nucleotides may be represented as A, AA, AAA, . . . , up to N sequential A nucleotides. Accurate quantification of homopolymer lengths (e.g., a number of sequential identical nucleotides in a sequence) may encounter challenges owing to random and unpredictable systematic variations in signal level, which can cause errors in quantifying the homopolymer length. In some cases, instrument and detection systematics can be calibrated and removed by monitoring instrument diagnostics and common-mode behavior across large numbers of colonies. Accurate quantification of homopolymer lengths (e.g., a number of sequential identical nucleotides in a sequence) may also encounter challenges owing to sequence context dependent signal, which may be different for every sequence. For example, in the case of fluorescence measurements of dilute labeled nucleotides, sequence context can affect both the number of labeled analogs (variable tolerance for incorporating labeled analogs) as well as fluorescence of individual labeled analogs (e.g., quantum yield of dyes affected by local context of ±5 bases, as described by [Kretschy, et al., Sequence-Dependent Fluorescence of Cy3- and Cy5-Labeled Double-Stranded DNA, *Bioconjugate Chem.*, 27(3), pp. 840-848], which is incorporated herein by reference in its entirety). In practice, with dye-terminator Sanger cycle sequencing, substantial systematic variations in signals have been identified for 3-base contexts (e.g., as described by [Zakeri, et al., Peak height pattern in dichloro-rhodamine and energy transfer dye terminator sequencing, *Biotechniques,* 25(3), pp. 406-10], which is incorporated herein by reference in its entirety). For example, FIG. 1 shows an example of reproducible fluorescent signal variations for 6 local contexts for a Cy5-labeled nucleotide analog.

The present disclosure provides methods and systems for context aware sequencing (e.g., suitable for flow SBS). The methods and systems may comprise encoded historical data and algorithmic steps to accurately and efficiently determine base calls and/or quantify homopolymer lengths from a given series of sequence signals corresponding to nucleotide flows. Such encoded historical data may be developed by deep learning on replicates of diverse sequence contexts using one or more sequencing chemistry variants (e.g., polymerases, labeled analogs, buffers, and conditions). The context awareness may comprise information associated with one or more nucleotide base positions, such as a given homopolymer being assessed, one or more bases prior to the given homopolymer, one or more bases following the given homopolymer, or any combination thereof.

In an aspect, disclosed herein is a method for quantifying context dependency of a plurality of sequence signals. Quantifying context dependency may comprise sequencing deoxyribonucleic acid (DNA) molecule(s) to provide a plurality of sequence signals, and in some cases, a plurality of imputed sequences. The DNA molecule(s) may comprise a known sequence. In some embodiments, the DNA molecules comprise synthetic templates (e.g., synthetic template DNA molecules). In some embodiments, the known sequences comprise one or more homopolymers of length N (where N may be at least 1 base, at least 2 bases, at least 3 bases, at least 4 bases, at least 5 bases, at least 6 bases, at least 7 bases, at least 8 bases, at least 9 bases, or at least 10 bases). In some embodiments, the plurality of imputed sequences comprises one or more homopolymers of length N (where N may be at least 1 base, at least 2 bases, at least 3 bases, at least 4 bases, at least 5 bases, at least 6 bases, at least 7 bases, at least 8 bases, at least 9 bases, or at least 10 bases). Next, context dependency may be quantified by determining an expected signal for each of one or more loci. The context dependency may be quantified based at least on (i) the plurality of sequence signals, (ii) the plurality of imputed sequences, (iii) the known sequence, or (iv) a combination thereof.

Identification of a local context may comprise aggregating a plurality of imputed sequences and their associated sequence signals. The plurality of imputed sequences and their associated sequence signals may then be stacked together, in some cases using alignment to a reference genome, in order to identify and group nucleotide bases associated with the same genomic positions. The plurality of imputed sequences and their associated sequence signals may be stacked together by comparison of the imputed sequences to each other to identify common local contexts. Alternatively, the plurality of imputed sequences and their associated sequence signals may be stacked together by alignment to a reference. For example, the plurality of imputed sequences (and their associated sequence signals) may be aligned to a reference genome. Alternatively, the plurality of sequence signals (and their associated imputed sequences) may be aligned to a reference signal. The stacked imputed sequences and their associated signals may be stacked together using any number of consecutive bases that are likely to contain context dependency, such as 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, or more than 20 bases.

Using these imputed sequences, which may be aggregated and grouped by an n-base context, a context model can be built and trained (e.g., by aggregating data for a particular genomic context to observe any systematic behavior) to learn how to interpret signals toward accurate base calling and/or determination of homopolymer lengths. Developing a context model may comprise analyzing the plurality of associated sequence signals to discover systematic behavior, and developing rules for predicting base calls and/or homopolymer lengths, based on correlations between context-dependent signals and imputed sequences, as described elsewhere herein. Such correlations, or context dependencies, may comprise a number of bases (e.g., 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, or more than 20 bases) prior to and/or after a given sequence or signal. For example, if an 'A' appears after a first sequence (e.g., 'TCTCG'), based on context dependency, a first signal level (e.g., 0.7 of the nominal signal) may be expected, and if the 'A' appears after a second sequence (e.g., 'AAACC'), a second signal level (e.g., 1.3 of the nominal signal may be expected). Such context dependency can be aggregated into a trained model to refine, for example, base calls and estimations of homopolymer lengths from imputed sequences and/or sequence signals.

For example, the context model may be built and trained (e.g., using machine learning techniques) based on analysis of imputed sequences and associated signals obtained by sequencing DNA molecules with known sequences (e.g., from synthetic template DNA molecules). Such a context model may comprise expected sequence signals (e.g., signal amplitudes) corresponding to an n-base portion of a locus (e.g., where N is at least 1 base, at least 2 bases, at least 3 bases, at least 4 bases, at least 5 bases, at least 6 bases, at least 7 bases, at least 8 bases, at least 9 bases, or at least 10 bases). Alternatively, or in addition, context models may comprise distributions, medians, averages, or other quantitative measures of sequence signals (e.g., signal amplitudes) corresponding to an n-base portion of a locus.

Methods and systems of the present disclosure may comprise algorithms that use only a sequence known a priori (e.g., a double-stranded sequence prior to the homopolymer), or simultaneously assessing a series of flow measurements to determine a series of homopolymer lengths comprising a sequence most likely to produce the observations (e.g., a maximum likelihood sequence determination). The algorithms may account for any label-label interactions, e.g. quenching, that may occur and influence the sequence signals. The algorithms may also account for any known position-dependent signal and/or any photobleaching effects that may occur and influence the sequence signals. For example, context dependency may be affected by flow sequencing of mixed populations of nucleotides (e.g., comprising natural nucleotides and modified nucleotides). Such mixed populations of nucleotides may compete for incorporation by a polymerase in a flow sequencing process, thereby giving rise to varying context-dependent sequence signals.

The algorithms may incorporate training data of known sequences comprising at one or more replicates of every context having significant correlation with homopolymer signal variation. Such incorporation may be repeated for every different discrete chemistry variant for which the algorithm is to be applied.

The algorithms may comprise auxiliary outputs, which may include assessments of the quantization noise (e.g., Poisson or binomial random variation) or other quality assessments, including a confidence interval or error assessment of the homopolymer length. The outputs may also may include dynamic assessments of chemistry process parameters (e.g., temperature) and the most likely labeling fraction to account for the observations as well.

The trained context model may then be applied by one or more trained algorithms (e.g., machine learning algorithms) to predict base calls and/or homopolymer lengths (such as, for example, of a plurality of imputed sequences and associated signals obtained by sequencing DNA molecules with unknown sequences). Such predictions may comprise refining or correcting base calls and/or homopolymer lengths of a plurality of imputed sequences. Alternatively, such predictions may comprise determining base calls and/or homopolymer lengths from a plurality of sequence signals. For example, a second set of DNA molecules comprising unknown sequences may be sequenced, thereby generating a second plurality of sequence signals and imputed sequences. Next, base calls of the second set of DNA molecules may be generated, e.g., based at least on (i) the second plurality of imputed sequences and/or sequence signals associated with the second plurality of sequence signals, (ii) the second plurality of imputed sequences, (iii) at least a portion of the expected signals, (iv) the known sequence, or (v) a combination thereof. Such predictions may be performed in real-time (e.g., as sequence signals are measured). Real-time can include a response time of less than 1 second, tenths of a second, hundredths of a second, a millisecond, or less. Real-time can include a simultaneous or substantially simultaneous process or operation (e.g., generating base calls) happening relative to another process or operation (e.g., measuring sequence signals). All of the operations described herein, such as training an algorithm, predicting and/or generating base calls and other operations, such as those described elsewhere herein, are capable of happening in real-time.

Methods for Homopolymer Calling

The present disclosure provides methods and systems for accurate and efficient base calling of sequences comprising homopolymers. Such base calling may be performed as part of a sequencing process, such as performing next-generation sequencing (e.g., sequencing by synthesis or flow sequencing) of nucleic acid molecules (e.g., DNA molecules). Such nucleic acid molecules may be obtained from or derived from a sample from a subject. Such a subject may have a disease or be suspected of having a disease. Methods and systems described herein may be useful for significantly reducing or eliminating errors in quantifying homopolymer lengths and errors associated with context dependence. Such methods and systems may achieve accurate and efficient base calling of homopolymers, quantification of homopolymer lengths, and quantification of context dependency in sequence signals.

The methods and systems provided herein may be used to directly call homopolymer lengths with high accuracy for each read. In addition, the methods and systems provided herein may comprise alignment of provisionally quantified reads (e.g., imputed sequences) containing homopolymers of uncertain length to a reference. Such alignment may be performed using an algorithm that places low penalty on homopolymer length errors. Using the statistical power of multiple aligned reads, the assessment of homopolymer lengths and uncertainties (e.g., confidence interval or error assessment), the methods and systems provided herein may determine the homopolymer lengths based on a consensus of all reads (e.g., for homozygous loci) or cluster reads. Alternatively or in combination, the methods and systems provided herein may make consensus calls on clusters (e.g., for heterozygous loci).

Figure 2:
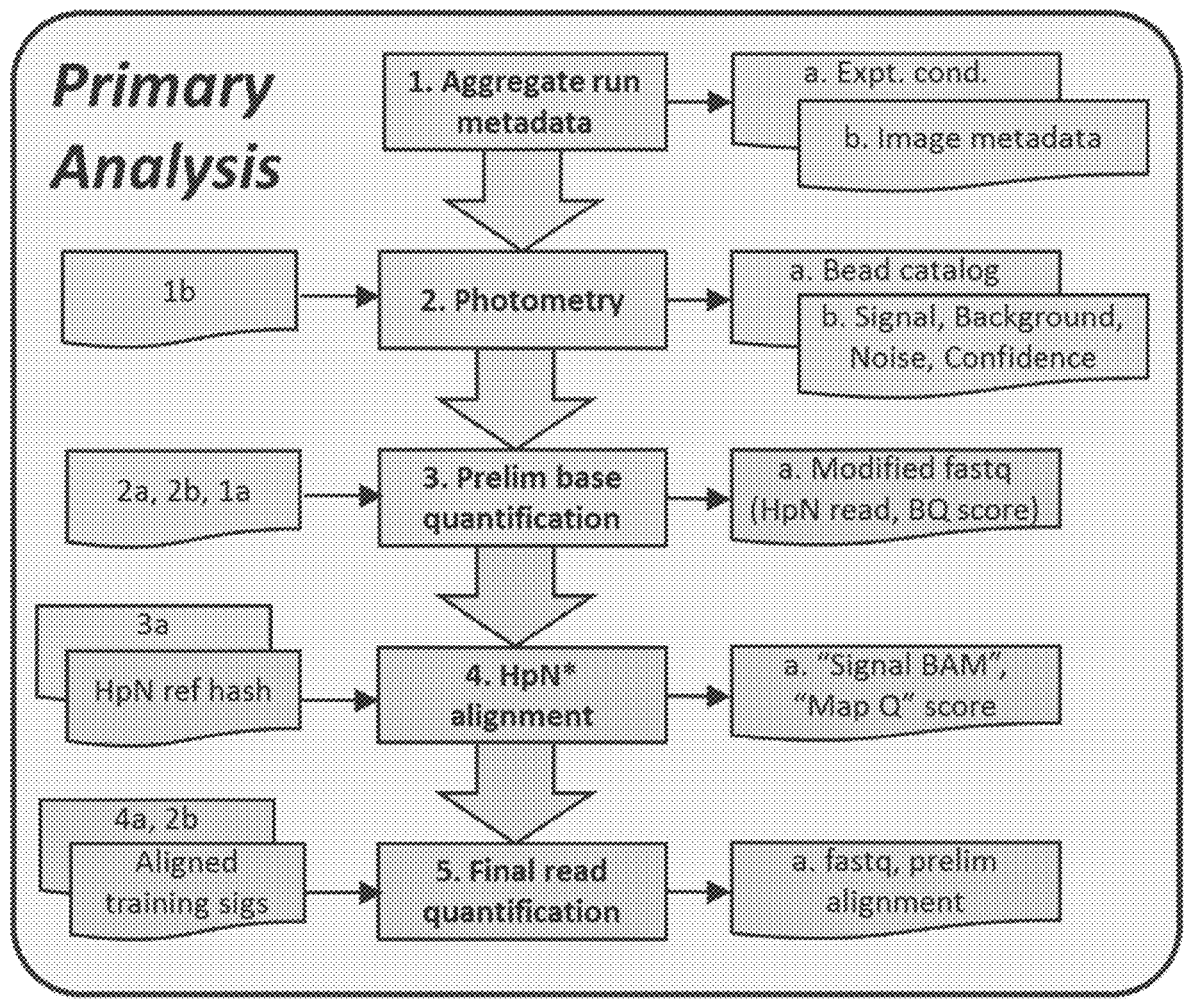
FIG. 2 shows a flowchart of primary analysis of sequence signals using alignment to a HpN truncated reference sequence.
Figure 3:
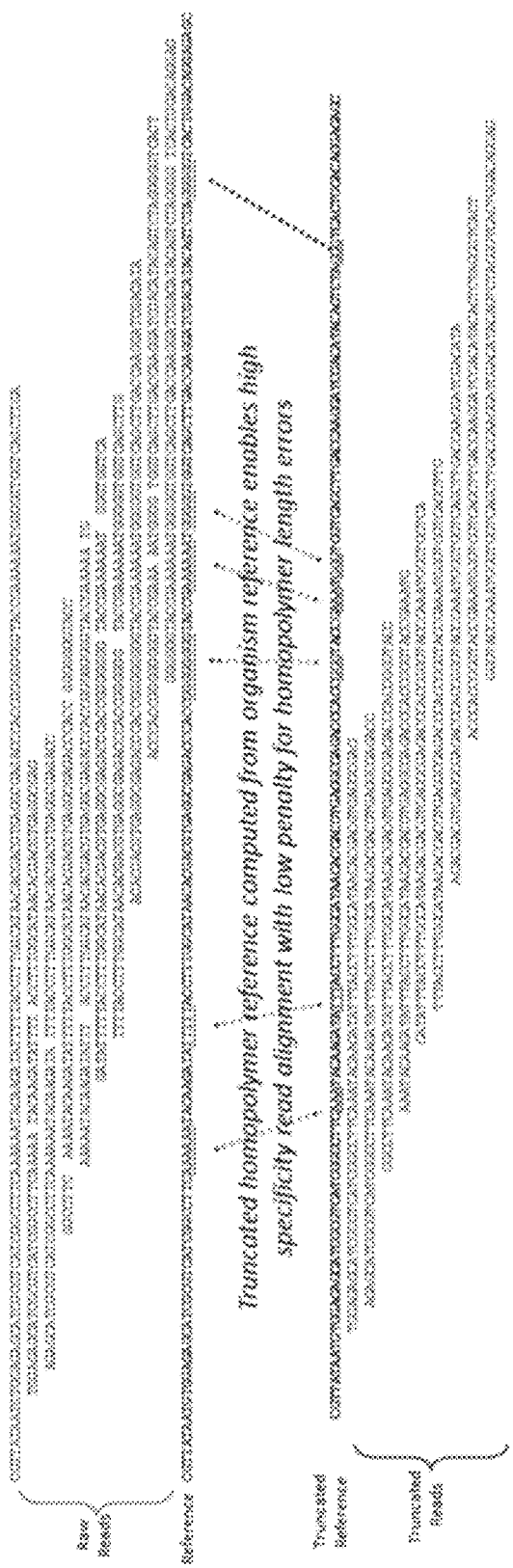
FIG. 3 shows an example of truncated homopolymer alignment, in which all identified homopolymers of length N or greater in a given sequence are truncated to a homopolymer of length N and then aligned to a reference.

In an aspect, disclosed herein is a method for processing a plurality of sequence signals. Such a method may be used to determine homopolymer lengths by consensus of aligned reads, as exemplified by FIG. 2, which shows a flowchart of primary analysis of sequence signals using alignment to a HpN truncated reference sequence. The method may comprise sequencing a nucleic acid sample to provide a plurality of sequence signals and imputed sequences. From such imputed sequences, homopolymer sequences (e.g., a sequence containing a homopolymer comprising multiple consecutive nucleotides of the same base) of at least N bases may be identified. These identified imputed homopolymer sequences may then be truncated to a homopolymer sequence of bases of length N, to yield one or more HpN truncated sequences. The length N may be any number of a plurality of bases, such as 2 bases, 3 bases, 4 bases, 5 bases, 6 bases, 7 bases, 8 bases, 9 bases, 10 bases, 11 bases, 12 bases, 13 bases, 14 bases, 15 bases, or more than 15 bases. FIG. 3 shows an example of truncated homopolymer alignment, in which all identified homopolymers of length N or greater in a given sequence are truncated to a homopolymer of length N and then aligned to a reference.

After truncation, the one or more HpN truncated sequences may be aligned to one or more truncated references. Such truncated references may be HpN truncated and thereby comprise one or more homopolymer sequences truncated to length N. After alignment of the one or more HpN truncated sequences, a consensus sequence may be generated from the one or more HpN truncated sequences aligned to the one or more HpN truncated references. Such a consensus sequence may comprise a homopolymer sequence of the length N. The consensus sequence may be generated based on the aligned HpN truncated sequences, the sequence signals associated with the aligned HpN truncated sequences, or a combination thereof.

In some embodiments, the method for processing a plurality of sequence signals may comprise calculating a length estimation error of the homopolymer sequence. The length estimation error may comprise a confidence interval for the length of the homopolymer sequence (homopolymer length). For example, the length estimation error for a homopolymer with an imputed length of 5 bases may comprise a confidence interval of [3, 7], or 5 bases±2 bases. The length estimation error may be calculated based at least on a distribution of signals or imputed homopolymer lengths of the one or more HpN truncated sequences aligned to the HpN truncated references.

In some embodiments, the method for processing a plurality of sequence signals may comprise pre-processing the plurality of sequence signals to remove systematic errors. Such pre-processing may be performed prior to truncating identified imputed homopolymer sequences and aligning the HpN truncated sequences to one or more truncated references. The pre-processing may be performed to address random and unpredictable systematic variations in signal level, which can cause errors in quantifying the homopolymer length. In some cases, instrument and detection systematic variation can be calibrated and removed by monitoring instrument diagnostics and common-mode behavior across large numbers of colonies.

In some embodiments, the method for processing a plurality of sequence signals may comprise determining lengths of the homopolymer sequences. This determining may be performed by determining the number of sequential nucleotides appearing in the consensus sequences generated from the aligned HpN truncated sequences associated with the plurality of sequence signals. This determining may be performed based at least on clustering of the homopolymer sequences or sequence signals associated with the homopolymer sequences.

In some embodiments, the plurality of sequence signals is generated by sequencing nucleic acids of a subject. The HpN truncated references may comprise an HpN truncated reference genome of a species of the subject (e.g., an HpN truncated human reference genome). In some cases, a number of lengths computed or classified when generating the consensus sequence may be restricted, based at least on the ploidy of the species of the subject. The plurality of sequence signals and/or imputed sequences may be generated by any suitable sequencing approach, such as massively parallel array sequencing, flow sequencing, sequencing by synthesis, or dye sequencing.

In another aspect, disclosed herein is a method for quantifying context dependency of a plurality of sequence signals and imputed sequences. Such a method may be used to quantify homopolymer lengths by extensive training with an essay on a known genome. The method may comprise sequencing deoxyribonucleic acid (DNA) molecules to provide a plurality of sequence signals and imputed sequences. In some cases, the DNA molecules comprise a known sequence. From such imputed sequences, homopolymer sequences (e.g., a sequence containing a homopolymer comprising multiple consecutive nucleotides of the same base) of at least N bases may be identified. These identified imputed homopolymer sequences may then be truncated to a homopolymer sequence of bases of length N, to yield one or more HpN truncated sequences. The length N may be any number of a plurality of bases, such as 2 bases, 3 bases, 4 bases, 5 bases, 6 bases, 7 bases, 8 bases, 9 bases, 10 bases, 11 bases, 12 bases, 13 bases, 14 bases, 15 bases, or more than 15 bases. After truncation, the one or more HpN truncated sequences may be aligned to one or more truncated references. Such truncated references may be HpN truncated and thereby comprise one or more homopolymer sequences truncated to length N. After alignment of the one or more HpN truncated sequences, context dependency of the associated sequence signals may be quantified. Such quantification may be based at least on (i) the one or more HpN truncated sequences aligned to the one or more HpN truncated references and/or sequence signals associated with the one or more HpN truncated sequences aligned to the HpN truncated references, (ii) the known sequence, or (iii) a combination thereof.

In some embodiments, the method for quantifying context dependency of a plurality of sequence signals and imputed sequences comprises sequencing a second set of DNA molecules comprising unknown sequences, thereby generating a second plurality of sequence signals and imputed sequences. From such imputed sequences, second homopolymer sequences (e.g., a sequence containing a homopolymer comprising multiple consecutive nucleotides of the same base) of at least N bases may be identified. These identified imputed second homopolymer sequences may then be truncated to a homopolymer sequence of bases of length N, to yield one or more second HpN truncated sequences. The length N may be any number of a plurality of bases, such as 2 bases, 3 bases, 4 bases, 5 bases, 6 bases, 7 bases, 8 bases, 9 bases, 10 bases, 11 bases, 12 bases, 13 bases, 14 bases, 15 bases, or more than 15 bases. After truncation, the one or more second HpN truncated sequences may be aligned to the one or more HpN truncated references. After alignment of the one or more HpN truncated sequences, homopolymer lengths of the second plurality of DNA molecules may be determined. Such determination may be based at least on (i) the one or more HpN truncated sequences aligned to the HpN truncated references and/or sequence signals associated with the one or more HpN truncated sequences aligned to the HpN truncated references, (ii) the quantified context dependency, or (iii) a combination thereof.

In some embodiments, the quantified context dependency is classified for a given context. Such a given context may be an n-base context, wherein 'n' is an integer greater than or equal to 2, an integer greater than or equal to 3, an integer greater than or equal to 4, an integer greater than or equal to 5, an integer greater than or equal to 6, an integer greater than or equal to 7, an integer greater than or equal to 8, an integer greater than or equal to 9, an integer greater than or equal to 10, an integer greater than or equal to 11, an integer greater than or equal to 12, an integer greater than or equal to 13, an integer greater than or equal to 14, an integer greater than or equal to 15, an integer greater than or equal to 16, an integer greater than or equal to 17, an integer greater than or equal to 18, an integer greater than or equal to 19, or an integer greater than or equal to 20.

Figure 4:
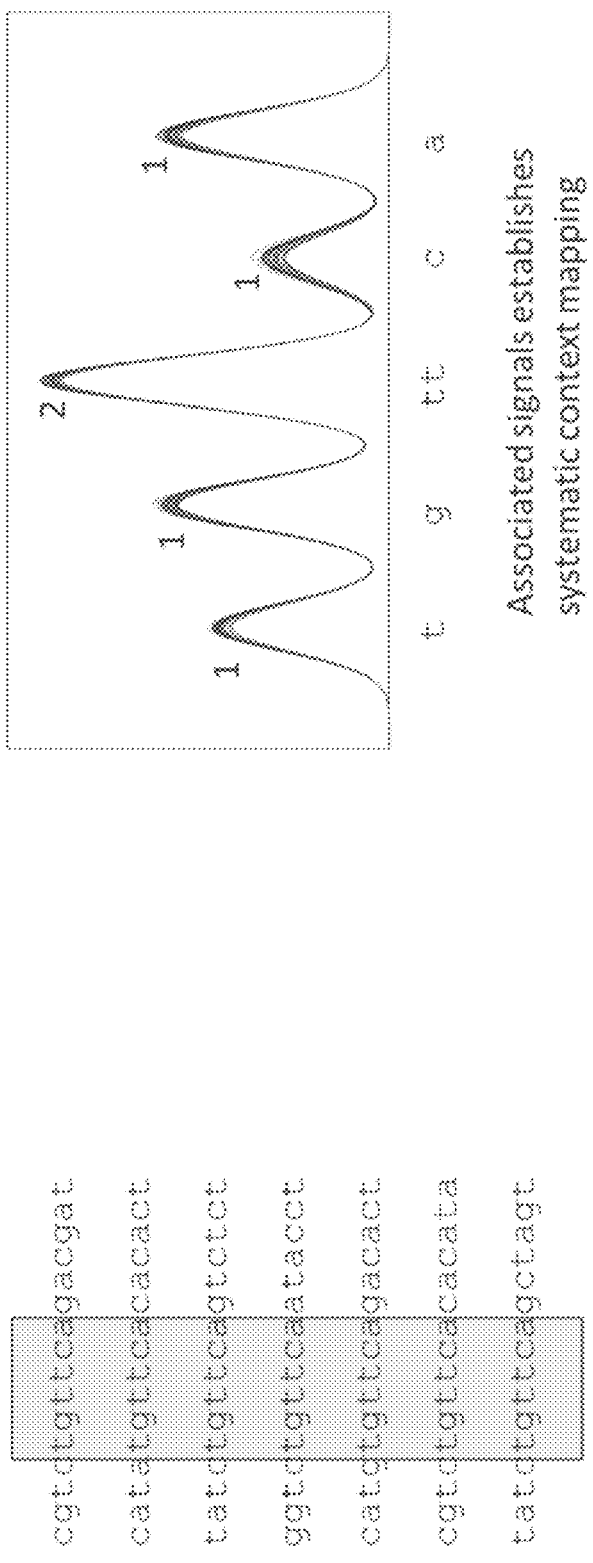
FIG. 4 shows an operation of local context identification and quantification, in which preliminary sequence calls are grouped by a 6-base context.

For example, as shown in FIG. 4, the quantified context dependency may be classified for a 6-base context, in which preliminary sequence calls (e.g., imputed sequences) are grouped by a 6-base context (in this example, "tgttca"). The associated signals of the imputed sequences grouped by the 6-base context are then used to establish a systematic context mapping. For example, representative signal measurements (signal levels) and signals variations thereof for the individual bases and homopolymers of the imputed sequences within the context (e.g., in this example, "t,", "g," "tt," "c," and "a," respectively) are measured and recorded as historical data. The historical data may be stored in one or more databases, individually or collectively. A database may comprise any data structure, such as a chart, table, list, array, graph, index, hash database, one or more graphics, or any other type of structure.

Figure 5:
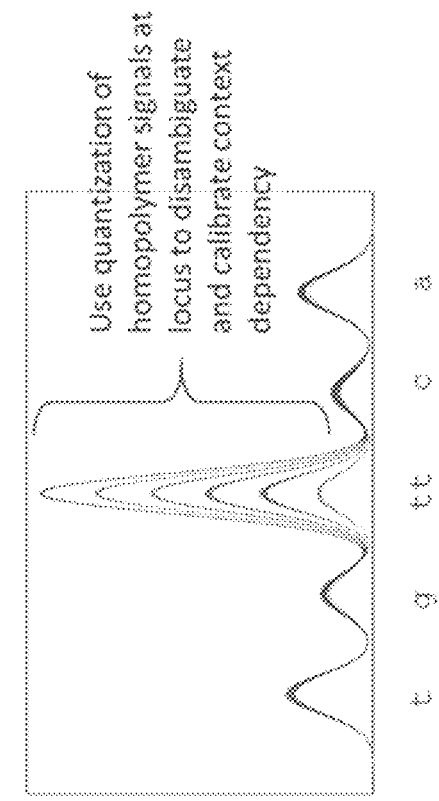
FIG. 5 shows an operation of local context identification and quantification, in which HpN truncated calls are grouped by a 6-base context.

As another example, as shown in FIG. 5, the quantified context dependency may be classified for a 6-base context, in which HpN truncated sequences are grouped by a 6-base context (in this example, "tgttca"). The associated signals of the HpN truncated sequences grouped by the 6-base context are then used to establish a systematic context mapping. For example, representative signal measurements (signal levels) and signals variations thereof for the individual bases and homopolymers of the HpN truncated sequences within the context (e.g., in this example, "t,", "g," "tt," "c," and "a," respectively) are measured and recorded as historical data (e.g., in a database of systems described herein).

Figure 6:
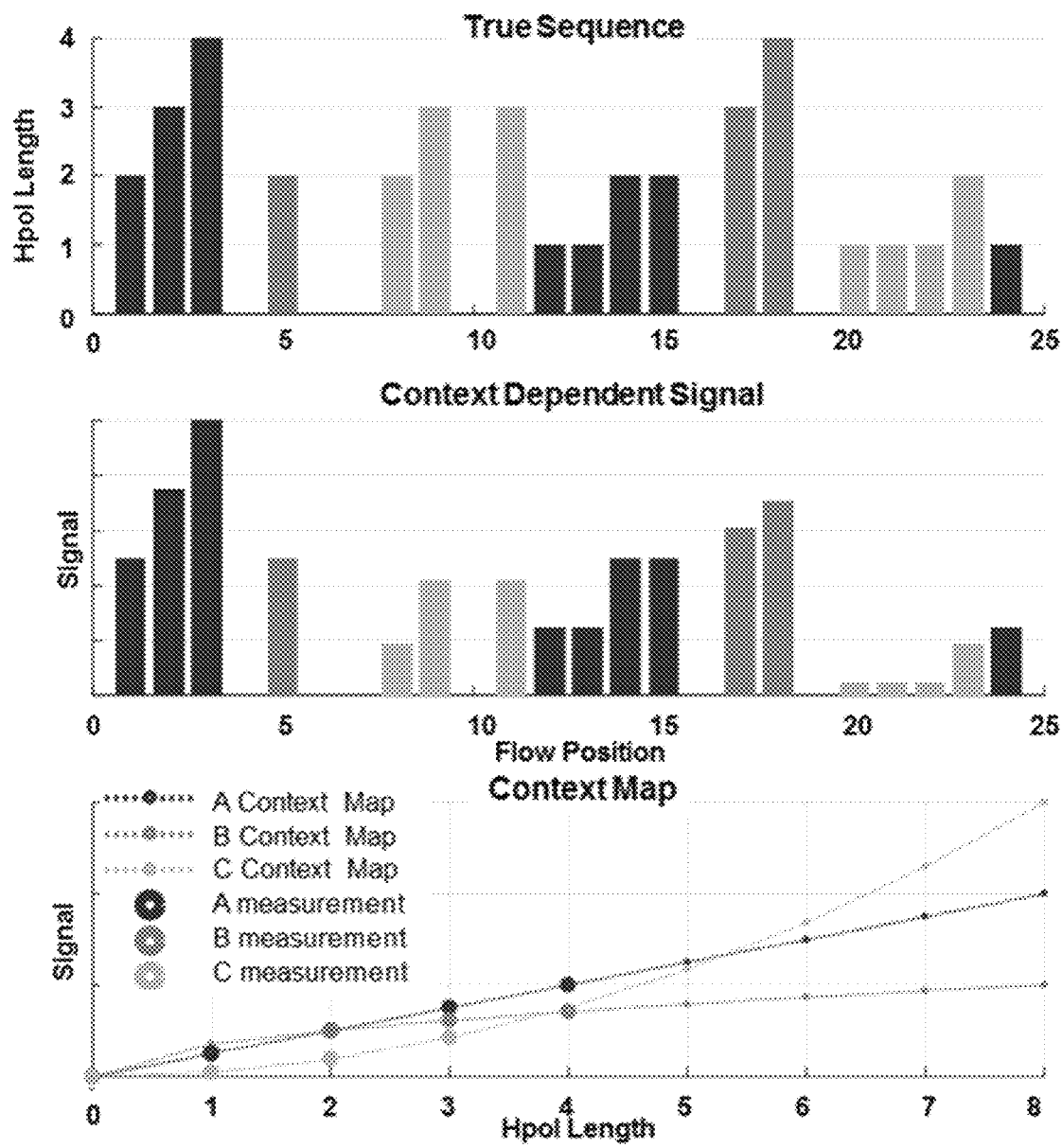
FIG. 6 shows an example of a context map, which includes a mathematical relationship between a signal and the number of consecutive nucleotides incorporated (e.g., homopolymer length) in a sequence.

FIG. 6 shows an example of a context map, which includes a mathematical relationship between a signal and the number of consecutive nucleotides incorporated (e.g., homopolymer length) in a sequence. Such a relationship may be represented as a context specific mapping (context map). As illustrated in FIG. 6, a comparison of the true sequences (which comprise homopolymers ranging in length from 2 to 4) and the associated context dependent signals of the true sequences indicates that there is not a perfectly linear relationship between a homopolymer's signal measurement (signal level) and the homopolymer's length, owing to context dependencies. This non-linear relationship can result in errors in imputed homopolymer lengths, which can then be corrected using historical data and context maps. The monotonic context (e.g., strictly increasing signal by homopolymer length) can be used to map each of a series of signals to correct homopolymer lengths. The context map may be used to train one or more algorithms (e.g., machine learning algorithms) to translate signals to predicted sequences and/or homopolymer lengths. For example, each local context that is found in an imputed sequence may be compared to an aggregated database to retrieve rules that can be applied for the translation.

In some embodiments, the DNA molecules are derived from ribonucleic acid (RNA) molecules. For example, the DNA molecules may be generated by performing reverse transcription on RNA molecules to generate complementary DNA (cDNA) molecules or derivatives thereof. The plurality of sequence signals and/or imputed sequences may be generated by any suitable sequencing approach, such as massively parallel array sequencing, flow sequencing, sequencing by synthesis, or dye sequencing. In some embodiments, quantifying the context dependency comprises establishing a relationship between signal amplitudes and homopolymer length for each of a plurality of loci. Such a relationship may be represented as a context specific mapping (context map).

In another aspect, disclosed herein is a method for quantifying context dependency of a plurality of sequence signals and imputed sequences. Such a method may comprise sequencing deoxyribonucleic acid (DNA) molecules to provide a plurality of sequence signals and imputed sequences. In some cases, the DNA molecules comprise a known sequence. From such imputed sequences, homopolymer sequences (e.g., a sequence containing a homopolymer comprising multiple consecutive nucleotides of the same base) of at least N bases may be identified. These identified imputed homopolymer sequences may then be truncated to a homopolymer sequence of bases of length N, to yield one or more HpN truncated sequences. The length N may be any number of a plurality of bases, such as 2 bases, 3 bases, 4 bases, 5 bases, 6 bases, 7 bases, 8 bases, 9 bases, 10 bases, 11 bases, 12 bases, 13 bases, 14 bases, 15 bases, or more than 15 bases. After truncation, the one or more HpN truncated sequences may be aligned to one or more truncated references. Such truncated references may be HpN truncated and thereby comprise one or more homopolymer sequences truncated to length N. After alignment of the one or more HpN truncated sequences, an expected signal for each of a plurality of loci in said HpN truncated references may be determined. Such expected signal may be determined based at least on (i) the one or more HpN truncated sequences aligned to the HpN truncated references and/or sequence signals associated with the one or more HpN truncated sequences aligned to the HpN truncated reference(s), (ii) said known sequence, or (iii) a combination thereof.

In some embodiments, the method for quantifying context dependency of a plurality of sequence signals and imputed sequences comprises sequencing a second set of DNA molecules comprising unknown sequences, thereby generating a second plurality of sequence signals and imputed sequences. From such imputed sequences, second homopolymer sequences (e.g., a sequence containing a homopolymer comprising multiple consecutive nucleotides of the same base) of at least N bases may be identified. These identified imputed second homopolymer sequences may then be truncated to a homopolymer sequence of bases of length N, to yield one or more second HpN truncated sequences. The length N may be any number of a plurality of bases, such as 2 bases, 3 bases, 4 bases, 5 bases, 6 bases, 7 bases, 8 bases, 9 bases, 10 bases, 11 bases, 12 bases, 13 bases, 14 bases, 15 bases, or more than 15 bases. After truncation, the one or more second HpN truncated sequences may be aligned to the one or more HpN truncated references. After alignment of the one or more HpN truncated sequences, homopolymer lengths of the second plurality of DNA molecules may be determined. Such determination may be based at least on (i) the one or more HpN truncated sequences aligned to the HpN truncated references and/or sequence signals associated with the one or more HpN truncated sequences aligned to the HpN truncated references, (ii) the quantified context dependency, or (iii) a combination thereof.

In some embodiments, the DNA molecules are derived from ribonucleic acid (RNA) molecules. For example, the DNA molecules may be generated by performing reverse transcription on RNA molecules to generate complementary DNA (cDNA) molecules or derivatives thereof. The plurality of sequence signals and/or imputed sequences may be generated by any suitable sequencing approach, such as massively parallel array sequencing, flow sequencing, sequencing by synthesis, or dye sequencing. In some embodiments, quantifying the context dependency comprises establishing a relationship between signal amplitudes and homopolymer length for each of a plurality of loci. Such a relationship may be represented as a context specific mapping (context map).

In another aspect, disclosed herein is a method for processing a plurality of sequence signals. Such a method may be used to determine homopolymer lengths by incorporation of secondary assay data. The method may comprise sequencing a nucleic acid sample to provide a plurality of sequence signals and imputed sequences. The plurality of sequence signals and imputed sequences may be processed to determine a set of one or more sequences comprising homopolymer sequences. The plurality of sequence signals and imputed sequences may also be processed to identify a presence and/or an estimated length of at least a portion of the homopolymer sequences. One or more algorithms may be used to identify the presence and/or the estimated length of the homopolymer sequences, by translating signals to homopolymer lengths (e.g., using a context map or other context dependency information). The estimated lengths of the homopolymer sequences may be refined using secondary assay data. Such secondary assay data may be used to provide or augment context dependency information. The plurality of sequence signals and/or imputed sequences may be generated by any suitable sequencing approach, such as massively parallel array sequencing, flow sequencing, sequencing by synthesis, or dye sequencing.

Methods for Analog Alignment

Figure 7:
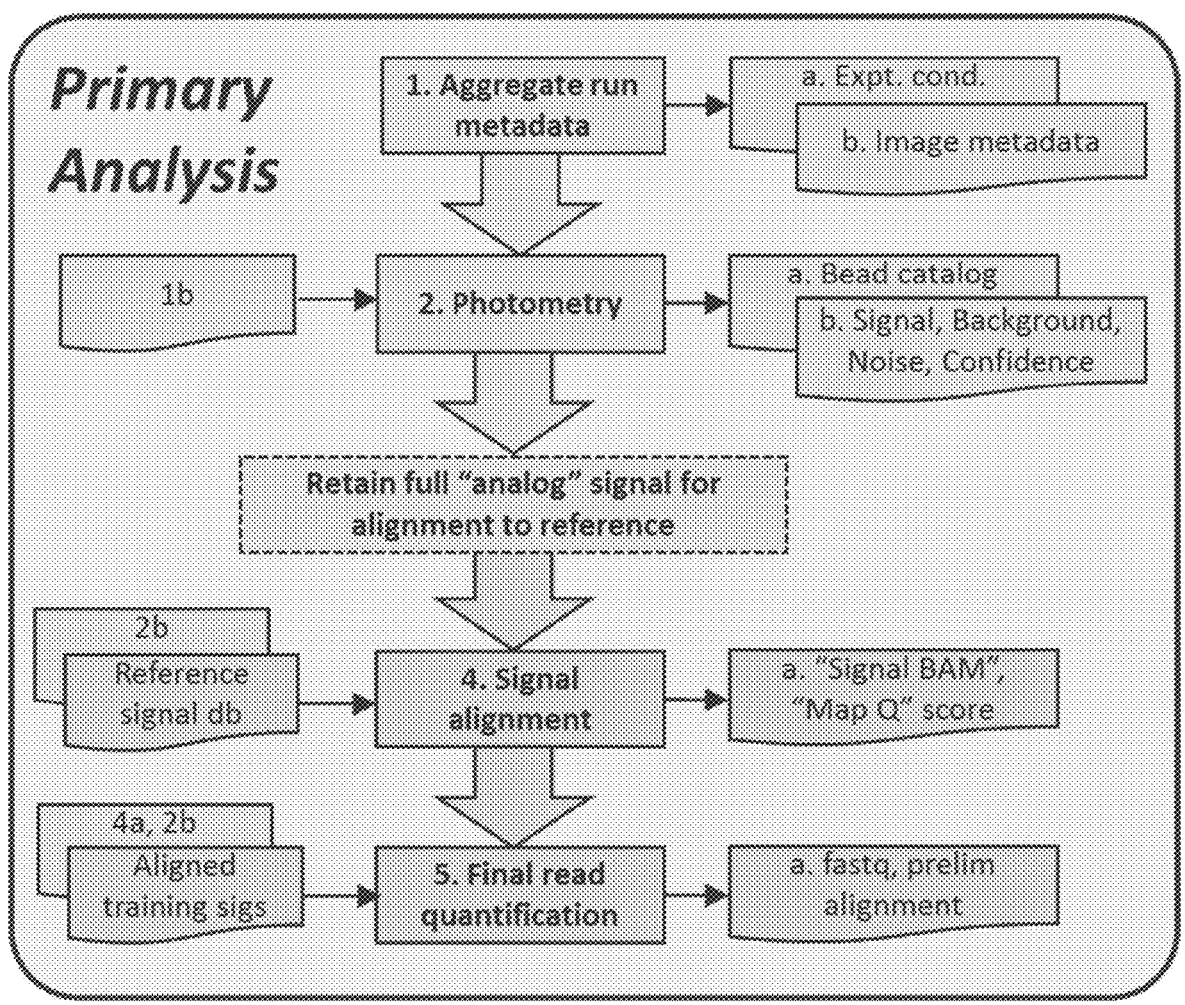
FIG. 7 shows a flowchart of primary analysis of sequence signals using alignment to an analog reference signal.

In another aspect, disclosed herein is a method for processing a plurality of sequence signals. Such a method may be used to determine homopolymer lengths by alignment of a signal to a reference signal (e.g., an analog reference signal), as exemplified by FIG. 7, which shows a flowchart of primary analysis of sequence signals using alignment to an analog reference signal. The method may comprise sequencing a nucleic acid sample to provide the plurality of sequence signals. The plurality of sequence signals may be aligned to a reference signal (e.g., an analog reference signal). Based at least on the aligned sequence signals, a reference locus comprising a homopolymer sequence may be identified. A consensus sequence may be generated from the plurality of sequence signals aligned to the reference signal. The consensus sequence may comprise a homopolymer sequence of N bases. The generation may be performed based at least on the identified reference locus, a length of the homopolymer sequence of said reference locus, and the reference signal (e.g., analog reference signal).

In some embodiments, the method for processing a plurality of sequence signals may comprise calculating a length estimation error of the homopolymer sequence. The length estimation error may comprise a confidence interval for the length of the homopolymer sequence (homopolymer length). For example, the length estimation error for a homopolymer with an imputed length of 5 bases may comprise a confidence interval of [3, 7], or 5 bases±2 bases. The length estimation error may be calculated based at least on a distribution of signals or imputed homopolymer lengths of the plurality of sequence signals aligned to the reference signal.

In some embodiments, the method for processing a plurality of sequence signals may comprise pre-processing the plurality of sequence signals to remove systematic errors. Such pre-processing may be performed prior to aligning the plurality of sequence signals to the reference signal. The pre-processing may be performed to address random and unpredictable systematic variations in signal level, which can cause errors in quantifying the homopolymer length. In some cases, instrument and detection systematic variation can be calibrated and removed by monitoring instrument diagnostics and common-mode behavior across large numbers of colonies.

In some embodiments, the plurality of sequence signals is generated by sequencing nucleic acids of a subject. In some cases, a number of lengths computed or classified when generating the consensus sequence may be restricted, based at least on the ploidy of the species of the subject. The plurality of sequence signals may be generated by any suitable sequencing approach, such as massively parallel array sequencing, flow sequencing, sequencing by synthesis, or dye sequencing.

In another aspect, disclosed herein is a method for quantifying context dependency of a plurality of sequence signals. The method may comprise sequencing deoxyribonucleic acid (DNA) molecules to provide the plurality of sequence signals. The DNA molecules may comprise a known sequence. The plurality of sequence signals may be aligned to a reference signal (e.g., an analog reference signal). The context dependency may be quantified in the plurality of sequence signals aligned to said reference signal. The quantification of context dependency may be performed based at least on the known sequence. In some embodiments, the aligning may comprise performing one or more analog signal processing algorithms.

In some embodiments, the method for quantifying context dependency of a plurality of sequence signals comprises sequencing a second set of DNA molecules comprising unknown sequences, thereby generating a second plurality of sequence signals. The second plurality of sequence signals may be aligned to the reference signal (e.g., analog reference signal). After alignment of the second plurality of sequence signals, homopolymer lengths of the second plurality of DNA molecules may be determined. Such determination may be based at least on the plurality of sequence signals aligned to said reference signal, the quantified context dependency, or a combination thereof.

In some embodiments, the DNA molecules are derived from ribonucleic acid (RNA) molecules. For example, the DNA molecules may be generated by performing reverse transcription on RNA molecules to generate complementary DNA (cDNA) molecules or derivatives thereof. The plurality of sequence signals and/or imputed sequences may be generated by any suitable sequencing approach, such as massively parallel array sequencing, flow sequencing, sequencing by synthesis, or dye sequencing. In some embodiments, quantifying the context dependency comprises establishing a relationship between signal amplitudes and homopolymer length for each of a plurality of loci. Such a relationship may be represented as a context specific mapping (context map).

In another aspect, disclosed herein is a method for quantifying context dependency of a plurality of sequence signals. The method may comprise sequencing deoxyribonucleic acid (DNA) molecules to provide the plurality of sequence signals. The DNA molecules may comprise a known sequence. The plurality of sequence signals may be aligned to a reference signal (e.g., an analog reference signal). After alignment of the plurality of sequence signals to a reference signal, an expected signal may be determined for each of a plurality of loci in the reference signal. The determination may be performed based at least on the plurality of sequence signals aligned to said reference signal, the known sequence, or a combination thereof. In some embodiments, the aligning may comprise performing one or more analog signal processing algorithms.

In some embodiments, the method for quantifying context dependency of a plurality of sequence signals comprises sequencing a second set of DNA molecules comprising unknown sequences, thereby generating a second plurality of sequence signals. The second plurality of sequence signals may be aligned to the reference signal (e.g., analog reference signal). After alignment of the second plurality of sequence signals, homopolymer lengths of the second plurality of DNA molecules may be determined. Such determination may be based at least on the plurality of sequence signals aligned to said reference signal, the quantified context dependency, or a combination thereof.

In some embodiments, the DNA molecules are derived from ribonucleic acid (RNA) molecules. For example, the DNA molecules may be generated by performing reverse transcription on RNA molecules to generate complementary DNA (cDNA) molecules or derivatives thereof. The plurality of sequence signals and/or imputed sequences may be generated by any suitable sequencing approach, such as massively parallel array sequencing, flow sequencing, sequencing by synthesis, or dye sequencing. In some embodiments, quantifying the context dependency comprises establishing a relationship between signal amplitudes and homopolymer length for each of a plurality of loci. Such a relationship may be represented as a context specific mapping (context map).

In another aspect, disclosed herein is a method for processing a plurality of sequence signals. The method may comprise sequencing a nucleic acid sample to provide the plurality of sequence signals. The plurality of sequence signals may be aligned to a reference signal (e.g., an analog reference signal). After aligning the plurality of sequence signals to a reference signal, a genomic locus comprising a homopolymer sequence may be identified. The identification may be performed based at least on the aligned sequence signals. The plurality of sequence signals aligned to the reference signal may be processed to identify a presence and/or an estimated length of the homopolymer sequence.

One or more algorithms may be used to identify the presence and/or the estimated length of the homopolymer sequences, by translating signals to homopolymer lengths (e.g., using a context map or other context dependency information). The estimated lengths of the homopolymer sequences may be refined using secondary assay data. Such secondary assay data may be used to provide or augment context dependency information. The plurality of sequence signals may be generated by any suitable sequencing approach, such as massively parallel array sequencing, flow sequencing, sequencing by synthesis, or dye sequencing.

Computer Control Systems

Figure 8:
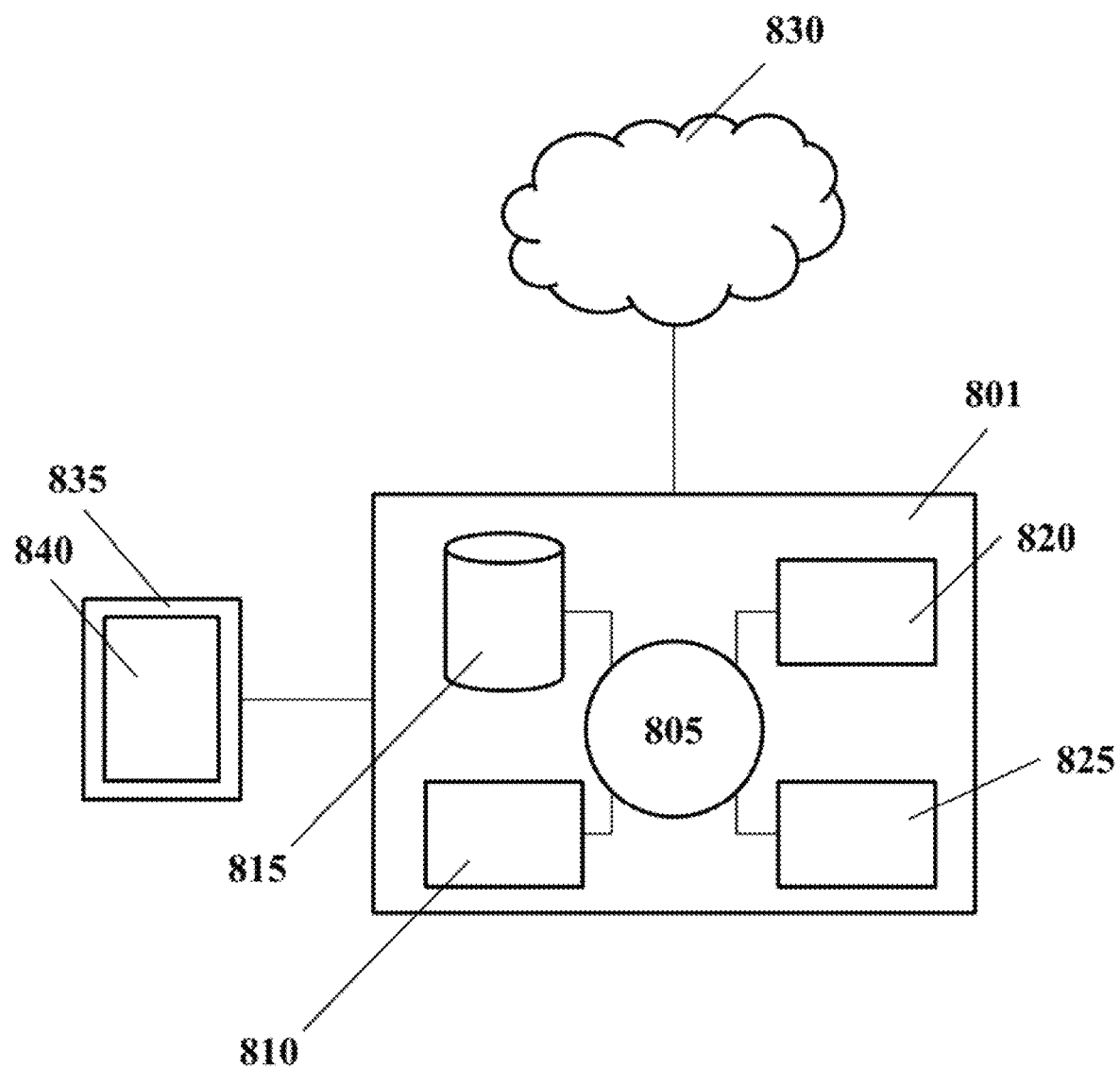
FIG. 8 shows a computer control system that is programmed or otherwise configured to implement methods provided herein.

The present disclosure provides computer control systems that are programmed to implement methods of the disclosure. FIG. 8 shows a computer system 801 that is programmed or otherwise configured to: process a plurality of sequence signals and/or imputed sequences, store a plurality of sequence signals and/or imputed sequences, perform HpN truncation of sequences, align sequences to a reference sequence, align signals to a reference signal, generate consensus sequences from aligned sequences, quantify context dependency (e.g., of sequence signals and/or imputed sequences), store training data (e.g., data comprising reference-aligned signals or context dependencies quantified from reference-aligned signals), determine expected signals for one or more loci, identify a presence and/or an estimated length of homopolymer sequences, translate signals to homopolymer lengths, and/or refine estimated homopolymer lengths using secondary assay data.

The computer system 801 can regulate various aspects of methods and systems of the present disclosure, such as, for example, processing a plurality of sequence signals and/or imputed sequences, storing a plurality of sequence signals and/or imputed sequences, performing HpN truncation of sequences, aligning sequences to a reference sequence, aligning signals to a reference signal, generating consensus sequences from aligned sequences, quantifying context dependency (e.g., of sequence signals and/or imputed sequences), storing training data (e.g., data comprising reference-aligned signals or context dependencies quantified from reference-aligned signals), determining expected signals for one or more loci, identifying a presence and/or an estimated length of homopolymer sequences, translating signals to homopolymer lengths, and/or refining estimated homopolymer lengths using secondary assay data.

The computer system 801 can be an electronic device of a user or a computer system that is remotely located with respect to the electronic device. The electronic device can be a mobile electronic device. The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840 for providing, for example, user selection of algorithms, signal data, sequence data, and databases. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805. The algorithm can, for example, process a plurality of sequence signals and/or imputed sequences, store a plurality of sequence signals and/or imputed sequences, perform HpN truncation of sequences, align sequences to a reference sequence, align signals to a reference signal, generate consensus sequences from aligned sequences, quantify context dependency (e.g., of sequence signals and/or imputed sequences), store training data (e.g., data comprising reference-aligned signals or context dependencies quantified from reference-aligned signals), determine expected signals for one or more loci, identify a presence and/or an estimated length of homopolymer sequences, translate signals to homopolymer lengths, and/or refine estimated homopolymer lengths using secondary assay data.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for processing a plurality of sequence signals, comprising:
a database that stores said plurality of sequence signals, said plurality of sequence signals generated upon sequencing of a nucleic acid; and
one or more computer processors coupled to said database, wherein said one or more computer processors are individually or collectively programmed to:
(a) align said plurality of sequence signals to a reference genome in a reference signal database, wherein the reference genome comprises reference signals;
(b) identify a reference locus comprising a homopolymer sequence based at least on said aligned sequence signals; and
(c) generate a consensus sequence from said plurality of sequence signals aligned to said reference signal, which consensus sequence comprises a homopolymer sequence of N bases, based at least on said identified reference locus, a length of said homopolymer sequence of said reference locus, and said reference signal.

2. The system of claim 1, wherein said one or more computer processors are individually or collectively programmed to calculate a length of estimation error of said homopolymer sequence, wherein said length of estimation error is calculated based at least in part on a distribution of signals or imputed homopolymer lengths of said plurality of aligned sequence signals.

3. The system of claim 1, wherein said one or more computer processors are individually or collectively programmed to pre-process said plurality of sequence signals to remove systematic error.

4. The system of claim 1, wherein said plurality of sequence signals are generated upon sequencing a nucleic acid molecule of a subject, and wherein said reference genome is a species of said subject.

5. The system of claim 4, wherein a number of lengths computed or classified is restricted based in part on a ploidy of said species of said subject.

6. The system of claim 1, wherein said plurality of sequence signals is generated at least in part by massively parallel array sequencing.

7. The system of claim 1, wherein said plurality of sequence signals is generated at least in part by flow sequencing.

8. The system of claim 1, wherein said reference signal comprises an analog reference signal, and wherein said one or more computer processors align said plurality of sequence signals by performing analog signal sequencing.

9. The system of claim 1, wherein said nucleic acid comprises a deoxyribonucleic acid (DNA).

10. The system of claim 1, wherein said nucleic acid comprises a ribonucleic acid (RNA).

11. A system for quantifying context dependency of a plurality of sequence signals, comprising:
a database that stores said plurality of sequence signals; and
one or more computer processors coupled to said database, wherein said one or more computer processors are individually or collectively programmed to:
(a) align said plurality of sequence signals to a reference genome in a reference signal database, wherein the reference genome comprises reference signals; and (b) quantify said context dependency in said plurality of sequence read signals aligned to said reference signal, based at least on a known sequence associated with said plurality of sequence signals.

12. The system of claim 11, wherein said reference signal comprises an analog reference signal, and wherein said one or more computer processors align said plurality of sequence signals by performing analog signal processing.

13. The system of claim 11, wherein said database stores a second plurality of sequence signals.

14. The system of claim 13, wherein said one or more computer processors are further individually or collectively programmed to:
   (a) align said second plurality of sequence signals to said reference signal, said second plurality of sequence signals generated upon sequencing a test nucleic acid sequence; and
   (b) determine homopolymer lengths of said second set of sequence molecules based at least on said plurality of sequence signals aligned to said reference signal and said quantified context dependency.

15. The system of claim 11, wherein said plurality of sequence signals are generated upon sequencing a nucleic acid.

16. The system of claim 15, wherein said nucleic acid comprises deoxyribonucleic acid (DNA).

17. The system of claim 15, wherein said nucleic acid comprises ribonucleic acid (RNA).

18. The system of claim 11, wherein said plurality of sequence signals is generated at least in part by massively parallel array sequencing, at least in part by flow sequencing, or at least in part by a combination thereof.

19. The system of claim 11, wherein said one or more computer processors establish a context-specific mapping between signal amplitudes and homopolymer lengths for each locus of a plurality of loci to quantify said context dependency.

20. The system of claim 11, wherein said one or more computer processors are further individually or collectively programmed to, for each plurality of loci in said reference signal, determine an expected signal for said locus based at least in part on said aligned sequence signals and said pre-determined sequence.

* * * * *